US010241105B2

(12) United States Patent
Kwak et al.

(10) Patent No.: US 10,241,105 B2
(45) Date of Patent: Mar. 26, 2019

(54) PORTABLE DEVICE HAVING EXHALATION SENSING FUNCTION

(71) Applicant: Samsung Electronics Co., Ltd., Suwon-si, Gyeonggi-do (KR)

(72) Inventors: Hyun-suk Kwak, Seoul (KR); Jang-pyo Park, Hwaseong-si (KR); Sang-hun Lee, Yongin-si (KR); Chang-hyun Kim, Seoul (KR); Jeong-eun Lee, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 243 days.

(21) Appl. No.: 15/180,682

(22) Filed: Jun. 13, 2016

(65) Prior Publication Data

US 2017/0212100 A1  Jul. 27, 2017

(30) Foreign Application Priority Data

Jan. 25, 2016  (KR) .................. 10-2016-0008902

(51) Int. Cl.
*G01N 33/497* (2006.01)
*A61B 5/08* (2006.01)
*A61B 5/00* (2006.01)
*H04M 1/725* (2006.01)
(Continued)

(52) U.S. Cl.
CPC .......... *G01N 33/497* (2013.01); *A61B 5/082* (2013.01); *A61B 5/6898* (2013.01); *A61B 5/742* (2013.01); *G01N 33/4972* (2013.01); *H04M 1/72527* (2013.01); *H04M 1/0241* (2013.01); *H04M 1/21* (2013.01)

(58) Field of Classification Search
CPC ..... G01N 33/4972; H04M 1/21; A61B 5/082; A61B 5/6898; A61B 5/742
USPC ...................... 73/23.3–23.34, 23.4
See application file for complete search history.

(56) References Cited

U.S. PATENT DOCUMENTS

| 6,726,636 B2 * | 4/2004 | Der Ghazarian .... B60K 28/063 422/84 |
| 2005/0053523 A1 * | 3/2005 | Brooke .............. G01N 33/4972 422/68.1 |

(Continued)

FOREIGN PATENT DOCUMENTS

| EP | 2 763 381 A1 | 8/2014 |
| EP | 2 620 768 B1 | 12/2014 |

(Continued)

OTHER PUBLICATIONS

"Ultra sonic motor moving", http://www.piezo-tech.com.
"Piezo Motor / Ultrasonic Stage Principle Animation", http://www.piezo-motor.net.

*Primary Examiner* — Lisa M Caputo
*Assistant Examiner* — Irving A Campbell
(74) *Attorney, Agent, or Firm* — Jefferson IP Law, LLP

(57) ABSTRACT

A portable device having an exhalation sensing function is provided. The portable device includes a gas detector that analyzes exhalation, and a device main body including a receiving portion in which the gas detector is received, the device main body having a call function, wherein, when a user makes a call using the device main body, the gas detector is automatically projected from the receiving portion of the device main body, and senses the user's exhalation.

20 Claims, 33 Drawing Sheets

(51) Int. Cl.
    *H04M 1/02*     (2006.01)
    *H04M 1/21*     (2006.01)

(56) References Cited

U.S. PATENT DOCUMENTS

| | | |
|---|---|---|
| 2010/0063408 A1* | 3/2010 | Nothacker ......... G01N 33/4972 600/532 |
| 2014/0076022 A1 | 3/2014 | Ohlsson et al. |
| 2014/0216136 A1 | 8/2014 | Yim |
| 2014/0223996 A1 | 8/2014 | Hunziker et al. |
| 2014/0234172 A1 | 8/2014 | Burgi et al. |
| 2014/0335905 A1 | 11/2014 | Bhoot |
| 2015/0237579 A1 | 8/2015 | Wu |

FOREIGN PATENT DOCUMENTS

| | | |
|---|---|---|
| JP | 2001-337064 A | 12/2001 |
| JP | 2005-72765 A | 3/2005 |
| KR | 10-2005-0090866 A | 9/2005 |
| KR | 10-2008-0017956 A | 2/2008 |
| KR | 10-1175514 B1 | 8/2012 |
| KR | 10-2013-0058187 A | 6/2013 |

\* cited by examiner

PORTABLE DEVICE HAVING EXHALATION SENSING FUNCTION

CROSS-REFERENCE TO RELATED APPLICATION(S)

This application claims the benefit under 35 U.S.C. § 119(a) of a Korean patent application filed on Jan. 25, 2016 in the Korean Intellectual Property Office and assigned Serial number 10-2016-0008902, the entire disclosure of which is hereby incorporated by reference.

TECHNICAL FIELD

The present disclosure relates to a portable device. More particularly, the present disclosure relates to a portable device having an exhalation sensing function that can automatically sense and analyze components of exhalation coming out from a user during a call.

BACKGROUND

As technology for portable devices, such as smart phones or cell phones has been developed, a variety of functions other than the phone call has been added to the portable device according to user's demand or need.

For example, a portable device capable of measuring the amount of alcohol by sensing exhalation of a person has been developed.

As one example, US Patent Application Publication No. US 2014/0216136 (SMART PHONE SENSOR PLATFORM, publication date: 2014 Aug. 7.) discloses a sensing device that can measure the amount of alcohol by using a smart phone. However, in this case since a breathmeter formed separately from the smart phone is required, there is a problem that it is inconvenient to carry both the smart phone and the breathmeter.

As another example, US Patent Application Publication No. US 2014/0234172 (PORTABLE ELECTRONIC DEVICE WITH BREATH ANALYZER, publication date: 2014 Aug. 21.) also discloses a smartphone capable of measuring the amount of alcohol. However, in this case, because a user is required to blow breath out into a measurement hole provided in the smartphone, there is a problem that the status of the user cannot be automatically detected from the user's exhalation.

Accordingly, development of portable devices that can automatically detect the status of a user from the user's exhalation even when the user is not aware of detecting the exhalation has been required.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a portable device having an exhalation sensing function that can automatically sense and analyze exhalation of a user without the user's awareness.

In accordance with an aspect of the present disclosure, a portable device having an exhalation sensing function is provided. The portable device includes a gas detector that analyzes exhalation, and a device main body including a receiving portion in which the gas detector is received, the device main body having a call function, wherein, when a user makes a call using the device main body, the gas detector is automatically projected from the receiving portion of the device main body, and senses the user's exhalation.

When the gas detector is projected from the device main body, a projecting portion of the gas detector may be inclined toward a mouth of the user.

The gas detector may be configured to project from a side of a mouthpiece portion of the device main body.

The gas detector may include a moving body slidingly disposed in the receiving portion of the device main body, and a gas sensor portion rotatably disposed in the moving body, and the device main body comprises a drive portion to move the moving body with respect to the receiving portion of the device main body, wherein when the gas detector is projected from the receiving portion of the device main body by the drive portion, the gas sensor portion is rotated a predetermined angle toward the mouthpiece portion of the device main body.

The gas sensor portion may include a sensor module that analyzes the exhalation, a short-range transceiver unit that transmits data measured by the sensor module to the device main body, a sensor battery that supplies an electric power to the sensor module and the short-range transceiver unit, and a housing that receives the sensor module, the short-range transceiver unit, and the sensor battery, the housing rotatably connected to the moving body.

The gas sensor portion may include a receiving coil for charging that charges the sensor battery, and the device main body may be provided with a transmitting coil for charging that supplies electricity to the receiving coil for charging.

When a battery of the device main body is charged, the transmitting coil for charging may supply electricity to the receiving coil for charging, thereby charging the sensor battery.

The gas sensor portion may include a microphone for measuring strength of the exhalation.

The sensor module may include at least one of a bad breath detection sensor, an alcohol detection sensor, a carbon monoxide detection sensor, a carbon dioxide detection sensor, a volatile organic compounds (VOCs) detection sensor, and a volatile sulfide compounds (VSCs) detection sensor.

The gas sensor portion may be configured to be rotated with respect to the moving body by a motor.

A torsion spring may be disposed between the gas sensor portion and the moving body.

The drive portion may include a sliding actuator disposed at a side of the moving body in the device main body, a plurality of bearings disposed opposite the sliding actuator in the device main body, and a plurality of elastic members disposed to press the plurality of bearings toward the moving body.

The drive portion may include a position detecting portion for detecting a position of the moving body.

A guide member may be disposed on a side surface of the moving body that is in contact with the sliding actuator.

The drive portion may include a drive roller that is disposed in the device main body and pressed in contact with one side surface of the moving body, a drive motor that rotates the drive roller, and a plurality of bearings that is disposed opposite the drive roller in the device main body and supports the moving body.

The device main body may include a controller for controlling the portable device, and when a call button or icon provided in the device main body is operated, the controller controls the drive portion to project the gas detector from the device main body.

The device main body may include a display portion for displaying information, and the controller outputs an analysis result of the exhalation detected by the gas detector to the display portion.

The device main body may include a memory for storing measurement data of the exhalation, and the controller may output exhalation measurement data of a certain period of time that is stored in the memory and comments for the exhalation measurement data to the display portion.

The moving body may include a stylus pen or a thermometer.

The portable device having an exhalation sensing function may include a foldable portable device.

In accordance with an aspect of the present disclosure, a portable device configured to perform an exhalation function is provided.

The portable device may perform the exhalation function and analyze the exhalation.

The portable device may perform a call function.

Other aspects, advantages and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, like reference numerals will be understood to refer to like parts, components and structures.

DETAILED DESCRIPTION

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
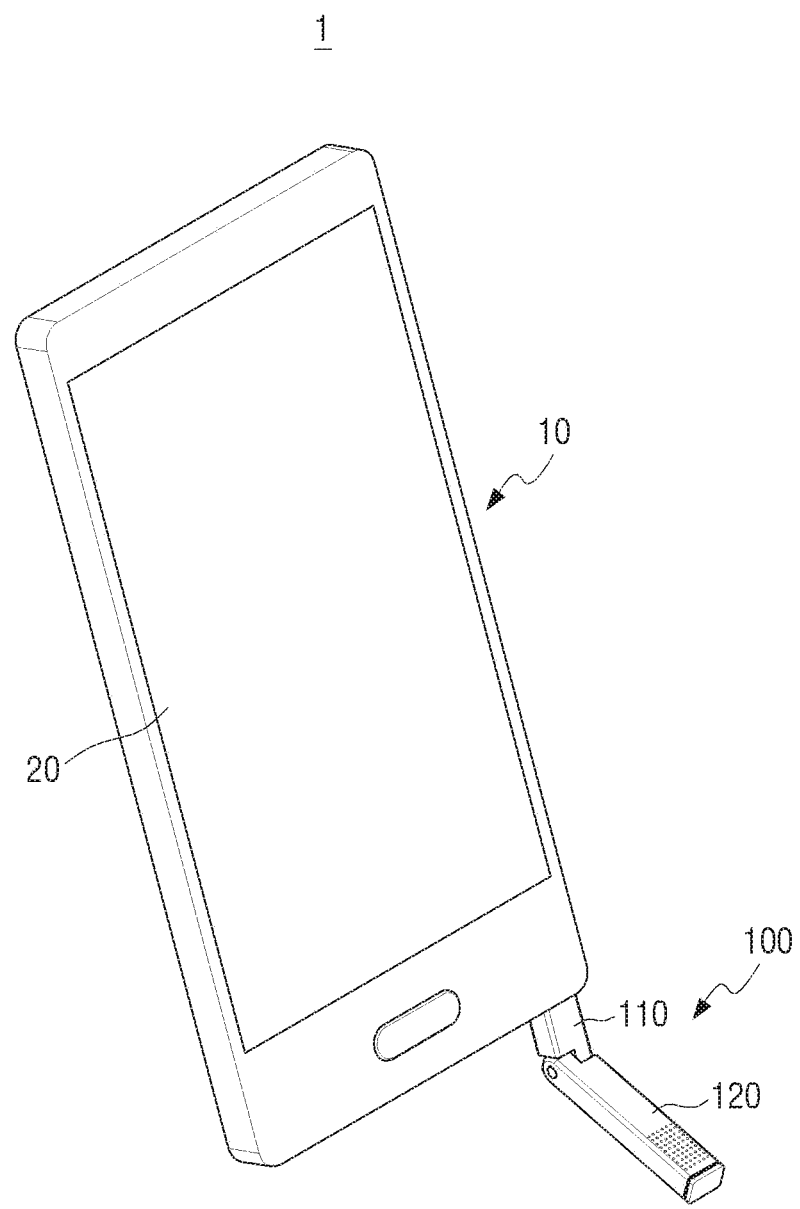
FIG. 1 is a perspective view illustrating a portable device having an exhalation sensing function according to an embodiment of the present disclosure.
Figure 2:
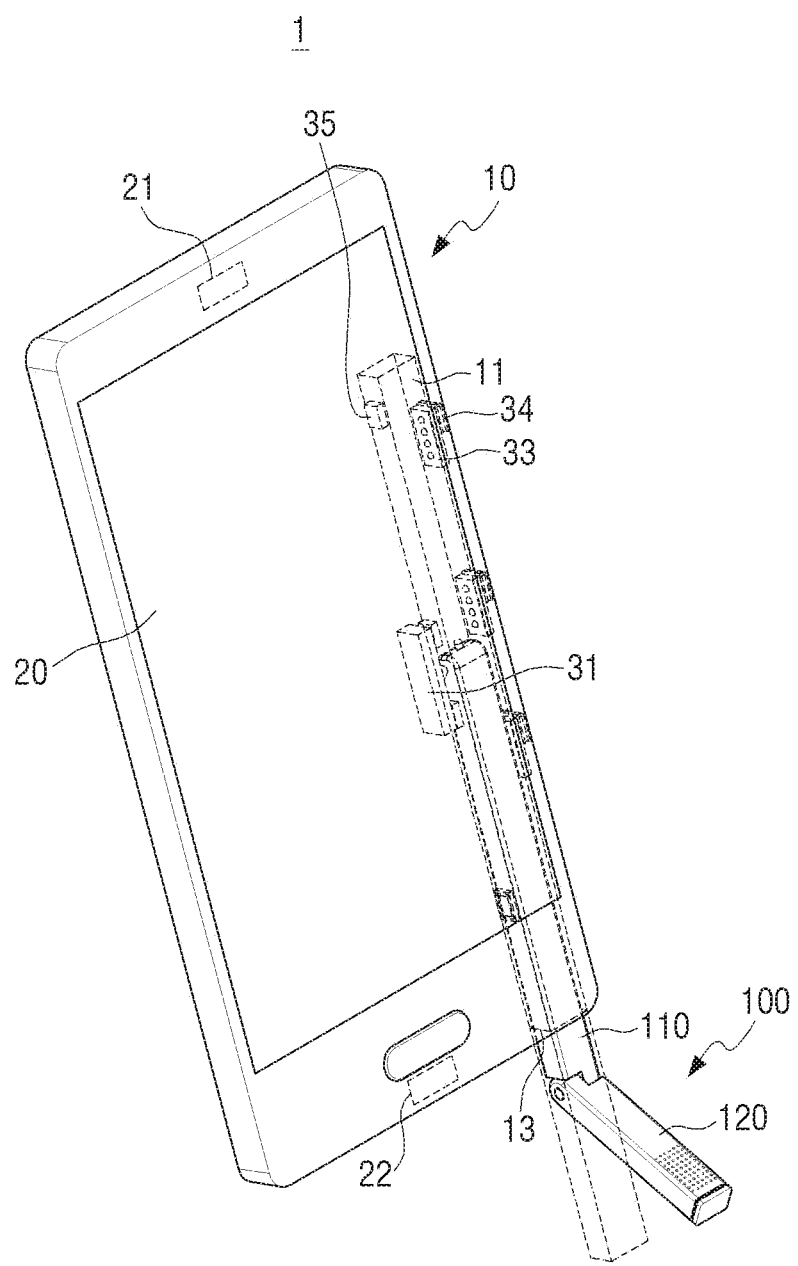
FIG. 2 is a perspective view illustrating a gas detector provided in the portable device having an exhalation sensing function of FIG. 1 according to an embodiment of the present disclosure.

FIG. 1 is a perspective view illustrating a portable device having an exhalation sensing function according to an embodiment of the present disclosure, and FIG. 2 is a perspective view illustrating a gas detector provided in the portable device having an exhalation sensing function of FIG. 1 according to an embodiment of the present disclosure.

Referring to FIGS. 1 and 2, a portable device having an exhalation sensing function 1 according to an embodiment of the present disclosure includes a device main body 10 and a gas detector 100. For reference, in the description of the present disclosure, the portable device 1 refers to a variety of portable equipment having a call function, such as smart phones, cell phones, and like.

The device main body 10 is configured to perform a call function, and includes a receiving portion 11 in which a gas detector 100 can be accommodated. In FIGS. 1 and 2, a smart phone is illustrated and explained as one example of the portable device 1; however, the present disclosure is not limited the smart phone.

A display portion 20 is provided on a front surface of the portable device 1. An earpiece portion 21 for generating a sound transmitted from the other side and a mouthpiece portion 22 for transmitting a user's voice are provided in both sides of the display portion 20 in the front surface of the portable device 1. While the earpiece portion 21 of the portable device 1 is located near an ear of the user and the mouthpiece portion 22 is located near a mouth of the user, the user talks on the portable device 1.

The receiving portion 11 in which the gas detector 100 can be received is provided inside the device main body 10. The receiving portion 11 is in communication with the outside through an opening 13 formed in a side surface of the device main body 10. Accordingly, the gas detector 100 may be received into and projected from the receiving portion 11 through the opening 13. The opening 13 of the receiving portion 11 is provided at one side of the mouthpiece portion 22 in the side surface of the portable device 1. Accordingly, the gas detector 100 projects from the one side of the mouthpiece portion 22 and senses the exhalation coming out from the mouth of the user during a call.

The gas detector 100 is formed to project from the device main body 10 of the portable device 1 and to sense the exhalation of the user while the user is talking on the portable device 1.

Hereinafter, a structure of the gas detector 100 will be described in detail with reference to FIGS. 3 to 5.

Figure 3:
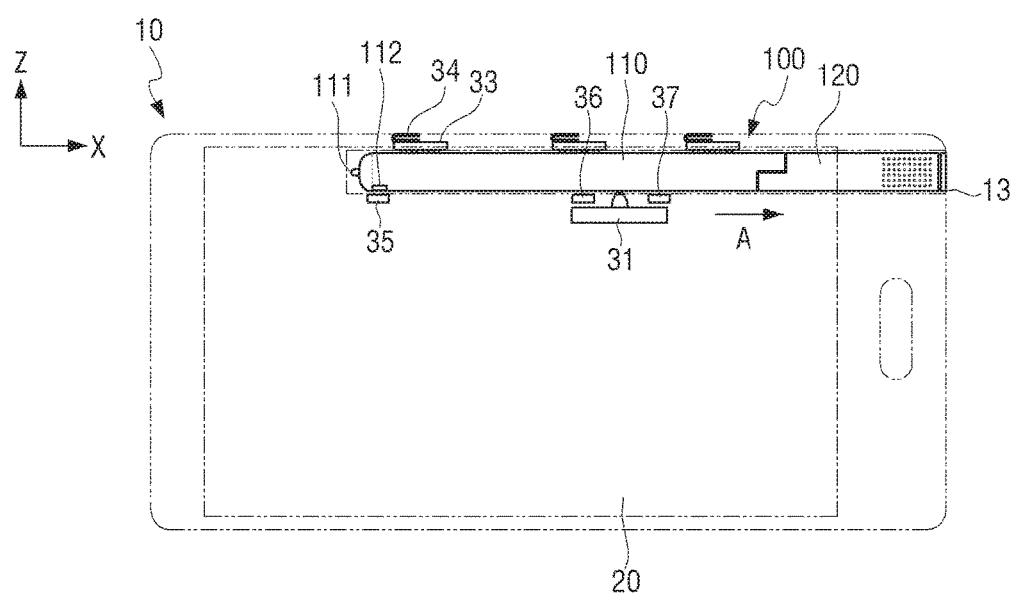
FIG. 3 is a view illustrating a state in which a gas detector is positioned at an original position in the portable device having an exhalation sensing function of FIG. 1 according to an embodiment of the present disclosure.
Figure 4A:
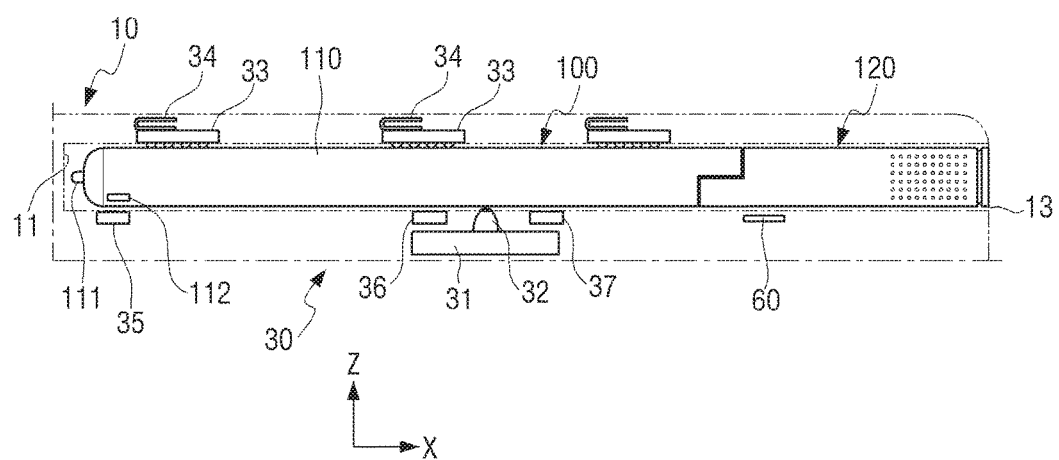
FIG. 4A is a partially enlarged view illustrating the gas detector of FIG. 3 according to an embodiment of the present disclosure.
Figure 4B:
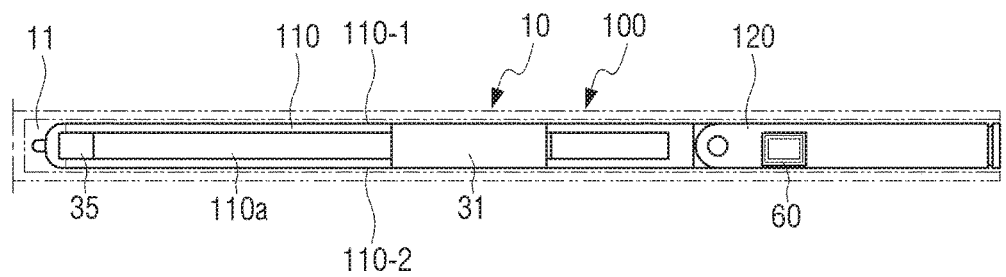
FIG. 4B is a side view illustrating the gas detector of FIG. 4A according to an embodiment of the present disclosure.

FIG. 3 is a view illustrating a state in which a gas detector is positioned at an original position in the portable device having an exhalation sensing function of FIG. 1 according to an embodiment of the present disclosure. FIG. 4A is a partial view enlargedly illustrating the gas detector of FIG. 3 according to an embodiment of the present disclosure, and FIG. 4B is a side view illustrating the gas detector of FIG. 4A according to an embodiment of the present disclosure. FIG. 5 is a view illustrating a state in which a gas detector projects from the portable device having an exhalation sensing function of FIG. 1 according to an embodiment of the present disclosure.

Figure 5:
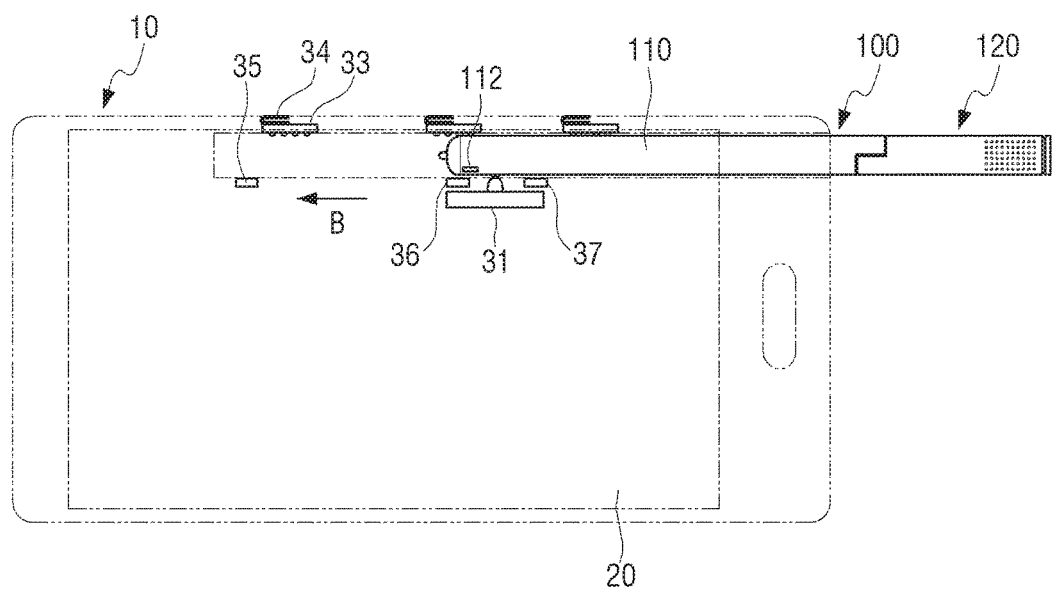
FIG. 5 is a view illustrating a state in which a gas detector projects from the portable device having an exhalation sensing function of FIG. 1 according to an embodiment of the present disclosure.

Referring to FIGS. 3 to 5, the gas detector 100 that is used in the portable device 1 according to an embodiment of the present disclosure may include a moving body 110 and a gas sensor portion 120.

The moving body 110 is disposed slidably in the receiving portion 11 of the device main body 10. The moving body 110 is formed substantially in a long rod shape having a rectangular cross-section. The moving body 110 is configured to support the gas sensor portion 120 so that when the gas sensor portion 120 is projected to the outside of the device main body 10, the gas sensor portion 120 is not separated from the device main body 10.

A space may be provided inside the moving body 110. Accordingly, components for performing different functions may be disposed inside the moving body 110. For example, the moving body 110 may be implemented to function as a stylus pen, a thermometer, etc. In the present embodiment of the present disclosure, since the moving body 110 is implemented as the stylus pen, as illustrated in FIGS. 4A and 4B, a nib 111 is protruded from one end of the moving body 110.

The gas sensor portion 120 is pivotably disposed at one end of the moving body 110, and is provided with a sensor to analyze the user's exhalation.

Hereinafter, the gas sensor portion 120 will be described in detail with reference to FIG. 6.

Figure 6:
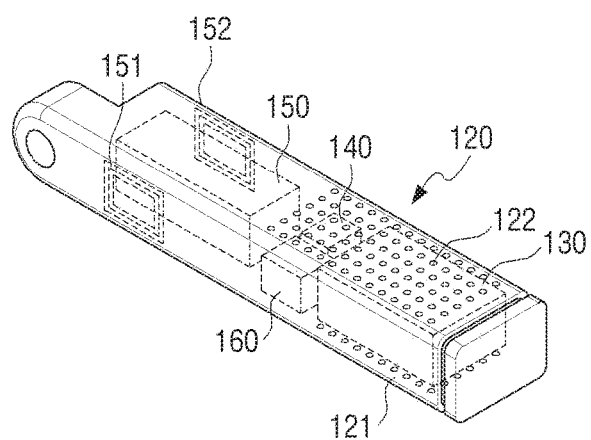
FIG. 6 is a perspective view illustrating a gas sensor portion of a gas detector of a portable device having an exhalation sensing function according to an embodiment of the present disclosure.

FIG. 6 is a perspective view illustrating a gas sensor portion of a gas detector of a portable device having an exhalation sensing function according to an embodiment of the present disclosure.

Referring to FIG. 6, the gas sensor portion 120 may include a sensor module 130, a short-range transceiver unit 140, a sensor battery 150, and a housing 121.

The sensor module 130 is configured to analyze the exhalation of the user, and to transmit analyzed data to the outside. In detail, the sensor module 130 may be formed to detect the kind and the amount of chemical components contained in the exhalation of the user using the principles of electrochemistry, infrared (IR), photoionization detection (PID), colorimetric, and the like, to convert the kind and the amount of the detected chemical components into an electric signal, and to output the electric signal. For example, the sensor module 130 may be configured to include at least one of a bad breath detection sensor, an alcohol detection sensor, a carbon monoxide detection sensor, a carbon dioxide detection sensor, and a volatile organic compounds (VOCs) detection sensor. Alternatively, the gas detector 100 may be configured so that the sensor module 130 includes only one sensor capable of sensing a single specific substance. At this time, the gas detector 100 may be replaced according to the application.

The bad breath detection sensor may be configured to detect the amount of volatile sulfide compounds (VSCs) associated with the halitosis (bad breath, or mouth smell) from the exhalation of a user. Accordingly, if using the bad breath detection sensor, the portable device 1 may detect the degree of the bad breath of the user, and inform the user about the degree of the bad breath.

The alcohol detection sensor is configured to detect the amount of alcohol from the exhalation of the user. Accordingly, if using the alcohol detection sensor, the portable device 1 may determine the user's drinking degree, and inform the user about the drinking degree.

The carbon monoxide detection sensor is formed to detect the amount of carbon monoxide contained in the exhalation of the user. The carbon dioxide detection sensor is formed to detect the amount of carbon dioxide contained in the exhalation of the user.

The VOCs detection sensor is configured to evaluate the air quality by identifying and analyzing concentration of VOCs in the air. Accordingly, if using the VOCs detection sensor, the portable device 1 may determine the status of air of the user's surroundings, and inform the user about the air status so that the user performs an action, such as ventilation, etc.

The short-range transceiver unit 140 is configured to transmit the data measured by the sensor module 130 to the device main body 10. The information detected by the sensor module 130 that is transmitted to the device main body 10 through the short-range transceiver unit 140 is received by a controller 50 that is disposed in the device main body 10. The controller 50 is configured so that the controller 50 determines a health condition of the user by analyzing the received information of the sensor module 130, and informs the user about the result through the display portion 20, etc.

The short-range transceiver unit 140 is configured to send and receive data to and from the controller 50 of the device main body 10 when the gas detector 100 projects from the device main body 10. Also, when the gas detector 100 is separated from the device main body 10, the short-range transceiver unit 140 is configured to send and receive data to and from the controller 50 of the device main body 10 within a predetermined distance. For example, the short-range transceiver unit 140 may use Bluetooth, WiFi, etc.

The sensor battery 150 is configured to supply electric power to the sensor module 130 and the short-range transceiver unit 140. The sensor battery 150 may use a disposable battery. However, in the present embodiment of the present disclosure, the sensor battery 150 may use a rechargeable battery. The rechargeable battery may be configured to be charged by using a charging cable. In the present embodiment of the present disclosure, the sensor battery 150 is implemented as the rechargeable battery capable of being charged by wireless charging.

For this, the gas sensor portion 120 may be provided with a receiving coil for charging 151 to charge the sensor battery 150, and the device main body 10 may be provided with a transmitting coil for charging 60 to supply electricity to the receiving coil for charging 151. In this embodiment of the present disclosure, as illustrated in FIG. 6, two receiving coils for charging 151 and 152 are disposed in the left and right of the sensor battery 150. The single transmitting coil for charging 60 is disposed to face one of the two receiving coils for charging 151 and 152 in the receiving portion 11 of the device main body 10. Accordingly, even when the gas detector 100 is inserted into the receiving portion 11 of the device main body 10 in an upside down state, the sensor battery 150 may be charged by the transmitting coil for charging 60 and the other receiving coil for charging 152 facing each other. Also, the controller 50 (see FIG. 10) of the device main body 10 may be configured so that when a battery 70 provided in the device main body 10 is charged, the controller 50 controls the transmitting coil for charging 60 to supply electricity to the receiving coils for charging 151 and 152, thereby charging the sensor battery 150.

The housing 121 forms an appearance of the gas sensor portion 120, and is configured to receive and support the sensor module 130, the short-range transceiver unit 140, and the sensor battery 150. Each of the top and bottom surfaces of the housing 121 is provided with a plurality of through holes 122. The sensor module 130 is provided below the plurality of through holes 122 so that sensor module 130 can analyze the exhalation incoming through the plurality of through holes 122.

One end of the housing 121 is rotatably coupled to one end of the moving body 110. For this, the one end of the housing 121 is provided with a first protruding portion 123, and a hinge hole is formed in the first protruding portion 123. The one end of the moving body 110 is provided with a second protruding portion 113 corresponding to the first protruding portion 123 of the housing 121, and a hinge hole is formed in the second protruding portion 113. Accordingly, when a hinge shaft 115 is inserted into the hinge hole of the first protruding portion 123 of the housing 121 and the hinge hole of the second protruding portion 113 of the moving body 110, the housing 121 can turn at a predetermined angle with respect to the moving body 110. At this time, the rotation angle of the housing 121 is limited by the shapes of the housing 121 and the moving body 110.

The gas sensor portion 120 may be provided with a microphone 160 for measuring the strength of exhalation. When using the microphone 160, the portable device 1 can measure the strength of the exhalation coming out from the user, and adjust timing when the sensor module 130 senses components of the exhalation. How to measure the exhalation using the microphone 160 will be described later.

Further, the gas sensor portion 120 may be formed so that when the gas sensor portion 120 is projected to the outside of the device main body 10, the gas sensor portion 120 automatically turns a certain angle with respect to the moving body 110. In other words, when a portion of the gas detector 100 projects from the receiving portion 11 of the device main body 10, the gas sensor portion 120 may be formed to turn a certain angle toward the mouthpiece portion 22 of the device main body 10. For example, the gas sensor portion 120 may be configured to be turned to a certain angle by using an elastic member. As another example, the gas sensor portion 120 may be configured to be turned by a motor so that the turning angle of the gas sensor portion 120 is controlled by the motor.

Hereinafter, a structure for turning a gas sensor portion with respect to the moving body using an elastic member will be described in detail with reference to FIGS. 7A to 7C.

Figure 7A:
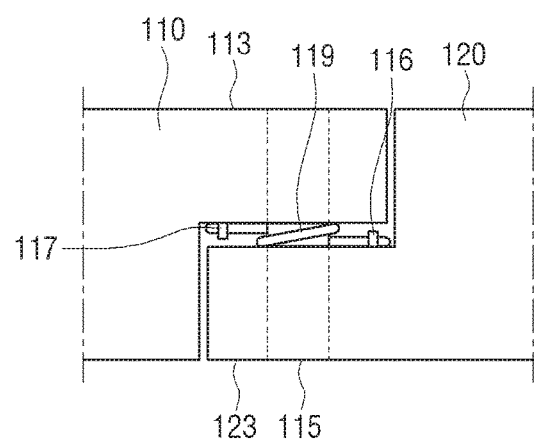
FIG. 7A is a partial view illustrating a connecting portion between a moving body and a gas sensor portion of a gas detector when the gas detector of a portable device having an exhalation sensing function according to an embodiment of the present disclosure is inserted in a device main body.

FIG. 7A is a partial view illustrating a connecting portion between a moving body and a gas sensor portion of a gas detector when the gas detector of a portable device having an exhalation sensing function according to an embodiment of the present disclosure is inserted in a device main body. FIG. 7B is a partial side view illustrating the connecting portion between the moving body and the gas sensor portion of the gas detector of FIG. 7A according to an embodiment of the present disclosure. FIG. 7C is a partial side view illustrating a state in which the gas sensor portion of the gas detector is turned a certain angle with respect to the moving body when the gas sensor portion of the gas detector of FIG. 7B projects from the device main body according to an embodiment of the present disclosure.

Figure 7B:
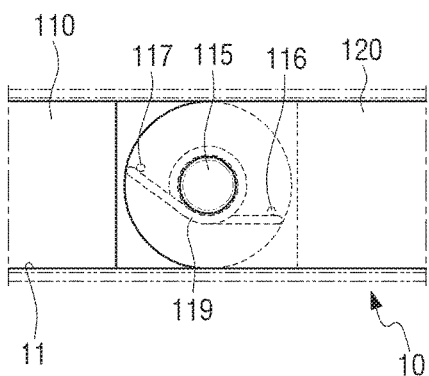
FIG. 7B is a partial side view illustrating the connecting portion between the moving body and the gas sensor portion of the gas detector of FIG. 7A according to an embodiment of the present disclosure.
Figure 7C:
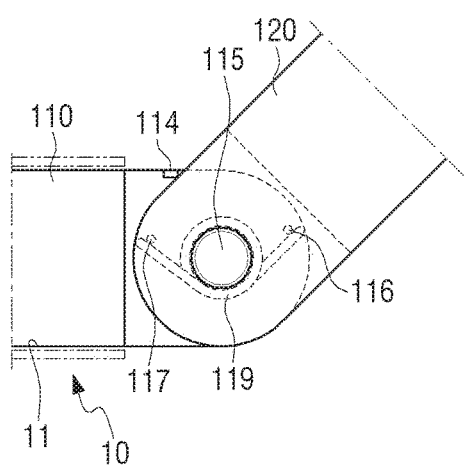
FIG. 7C is a partial side view illustrating a state in which the gas sensor portion of the gas detector is turned a certain angle with respect to the moving body when the gas sensor portion of the gas detector of FIG. 7B projects from the device main body according to an embodiment of the present disclosure.

Referring to FIGS. 7A to 7C, a torsion spring 119 is provided in a connecting portion between the moving body 110 and the gas sensor portion 120 of the portable device 1 according to an embodiment of the present disclosure. The torsion spring 119 is disposed on the hinge shaft 115, which is inserted in the hinge hole of the first protruding portion 123 of the gas sensor portion 120 and the hinge hole of the second protruding portion 113 of the moving body 110, between the first protruding portion 123 of the gas sensor portion 120 and the second protruding portion 113 of the moving body 110. Movement of one end of the torsion spring 119 is limited by a first fixing protrusion 116 provided on the first protruding portion 123 of the gas sensor portion 120, and movement of the other end of the torsion spring 119 is limited by a second fixing protrusion 117 provided on the second protruding portion 113 of the moving body 110.

When the gas detector 100 is received in the receiving portion 11 of the device main body 10, as illustrated in FIG. 7B, movement of the moving body 110 and the gas sensor portion 120 is blocked by the inner wall of the receiving portion 11 so that the torsion spring 119 maintains an extended state.

When the gas detector 100 is projected from the device main body 10, there is no force restricting the movement of the gas sensor portion 120 so that the gas sensor portion 120 is turned at a predetermined angle by the torsion spring 119 as illustrated in FIG. 7C. The turning angle of the gas sensor portion 120 may be limited by a stopper 114 provided in the moving body 110.

Hereinafter, a structure for turning a gas sensor portion a predetermined angle using a motor will be described in detail with reference to FIG. 8.

Figure 8:
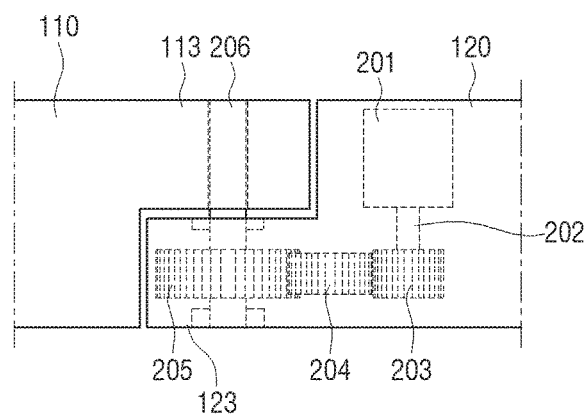
FIG. 8 is a partial view illustrating another example of a connecting portion between a moving body and a gas sensor portion of a gas detector of a portable device having an exhalation sensing function according to an embodiment of the present disclosure.

FIG. 8 is a partial view illustrating another example of a connecting portion between a moving body and a gas sensor portion of a gas detector of a portable device having an exhalation sensing function according to an embodiment of the present disclosure.

Referring to FIG. 8, a turning motor 201 is provided inside the housing 121 of the gas sensor portion 120. A shaft 206 is rotatably disposed in the first protruding portion 123 of the housing 121. Since the shaft 206 and the turning motor 201 are connected by a power transmission member, when the turning motor 201 rotates, the shaft 206 is rotated. For example, a drive gear 205 may be disposed in a portion of the shaft 206 that is located within the first protruding portion 123, and a pinion 203 may be provided in a shaft 202 of the turning motor 201. An intermediate gear 204 may be provided between the pinion 203 and the drive gear 205. Accordingly, when the turning motor 201 rotates, power of the turning motor 201 is transmitted to the drive gear 205 through the pinion 203 and the intermediate gear 204 so that the shaft 206 is rotated.

The second protruding portion 113 of the moving body 110 is fixed to a portion of the shaft 206 projected to the outside of the first protruding portion 123. The shaft 206 and the second protruding portion 113 of the moving body 110 are fixed so as not to rotate with respect to each other. Accordingly, when the shaft 206 is rotated by the turning motor 201, the moving body 110 is rotated. When the moving body 110 is received in the device main body 10 so that the moving body 110 cannot be rotated, the gas sensor portion 120 can be rotated with respect to the moving body 110. Accordingly, the controller 50 provided in the device main body 10 controls the turning motor 201, thereby controlling the rotation angle of the gas sensor portion 120.

The turning motor 201 may be powered from the sensor battery 150 provided in the gas sensor portion 120.

In the above description, the rotational force of the turning motor 201 is transmitted to the shaft 206 using one intermediate gear 204. However, this structure is only one example; therefore, the power transmission structure for transmitting the rotational force of the turning motor 201 to the shaft 206 may be variously formed.

The gas sensor portion 120 may be moved by a drive portion 30 that is provided in the receiving portion 11 of the device main body 10. The drive portion 30 is formed to linearly move the moving body 110 with respect to the receiving portion 11 of the device main body 10. The drive portion 30 will be described in detail with reference to FIGS. 4A and 4B.

Referring to FIGS. 4A and 4B, the drive portion 30 may include a sliding actuator 31, a plurality of bearings 33, and a plurality of elastic members 34.

The sliding actuator 31 is disposed at one side of the receiving portion 11 of the device main body 10, and generates a driving force to linearly move the moving body 110 with respect to the device main body 10. In the present embodiment of the present disclosure, the sliding actuator 31 uses a piezoelectric motor. A tip 32 of the piezoelectric motor 31 is in contact with one side surface of the moving body 110. The piezoelectric motor 31 includes two piezoelectric members having different phases so that when two piezoelectric members are driven, the tip 32 is moved in the X-Z direction. The moving body 110 is linearly moved with respect to the device main body 10 by the movement of the tip 32 of the piezoelectric motor 31.

For this, a guide member 110a may be provided on the one side surface of the moving body 110 with which the tip 32 of the piezoelectric motor 31 is in contact. The guide member 110a is formed in a thin strip shape, and formed of a wear resistant material. For example, the guide member 110a may be formed of a rigid metal material or a ceramic material, such as a zirconia ($ZrO_2$). When the guide member 110a with the wear resistance is disposed on the one side surface of the moving body 110, even if the gas detector 100 is used for a long time, the moving body 110 may be prevented from being worn by friction between the tip 32 of the piezoelectric motor 31 and the moving body 110. In the present embodiment of the present disclosure, the piezoelectric motor 31 is used as an example of the sliding actuator 31. However, this is only one example; the sliding actuator 31 is not limited to the piezoelectric motor.

The plurality of bearings 33 is provided opposite the sliding actuator 31 in the receiving portion 11 of the device main body 10 so as to face the other side surface of the moving body 110, and guides the moving body 110 of the gas detector 100 to be linearly moved by the sliding actuator 31. The plurality of bearings 33 may use a variety of bearings as long as they can guide the linear movement of the moving body 110.

The plurality of elastic members 34 is disposed in the receiving portion 11 of the device main body 10 to press the plurality of bearings 33 toward the moving body 110. In other words, the plurality of elastic members 34 presses the plurality of bearings 33 to cause a predetermined preload to be applied between the tip 32 of the piezoelectric motor 31 and the moving body 110 supported by the plurality of bearings 33, thereby generating a predetermined friction resistance between the tip of the piezoelectric motor 31 and the guide member 110a of the moving body 110. As described above, if there is a predetermined friction resistance between the tip 32 of the piezoelectric motor 31 and the guide member 110a of the moving body 110, the moving body 110 may be smoothly moved by the tip 32 of the piezoelectric motor 31. In this embodiment of the present disclosure, the plurality of elastic members 34 uses leaf springs. However, this is only one example. The plurality of elastic members 34 may use various type of springs as long as they can press the plurality of bearings 33 toward the moving body 110.

The drive portion 30 may include a position detecting portion for detecting a position of the moving body 110. The position detecting portion is configured to determine whether the moving body 110 is located in the receiving portion 11 or the rear end of the moving body 110 passes by the sliding actuator 31. For example, the position detecting portion may be configured of a plurality of hall sensors 35, 36, and 37 and a permanent magnet 112 that can be detected by the hall sensors 35, 36, and 37. The permanent magnet 112 is disposed in one end of the moving body 110, that is, opposite the other end of the moving body 110 in which the gas sensor portion 120 is disposed. The plurality of hall sensors 35, 36, and 37 is disposed in the receiving portion 11 of the device main body 10 to detect the permanent magnet 112 provided in the moving body 110.

In the present embodiment of the present disclosure, the position detecting portion is configured of three hall sensors, that is, a first hall sensor 35, a second hall sensor 36, and a third hall sensor 37. The first hall sensor 35 is disposed to detect the gas detector 100 positioned in a receiving position of the device main body 10. In detail, the first hall sensor 35 is disposed at a position facing the permanent magnet 112 of the gas detector 100 positioned in the receiving position.

The second hall sensor 36 and the third hall sensor 37 are disposed in opposite sides of the sliding actuator 31. The second hall sensor 36 is disposed to limit the moving distance of the moving body 110. In other words, the second hall sensor 36 is disposed to detect the permanent magnet 112 provided in the moving body 110 when the gas sensor portion 120 of the moving body 110 is projected a predetermined length from the device main body 10 so that the gas sensor portion 120 can be turned a certain angle with respect to the moving body 110. Accordingly, when the permanent magnet 112 of the moving body 110 comes to the position facing the second hall sensor 36, the gas sensor portion 120 is fully exposed from the device main body 10 and can be turned a certain angle with respect to the moving body 110.

The third hall sensor 37 is disposed between the tip 32 of the sliding actuator 31 and the opening 13 of the device main body 10, and detects one end of the gas detector 100 which is being inserted into the opening 13 of the device main body 10. The third hall sensor 37 may be disposed adjacent to the tip 32 of the sliding actuator 31.

When the second hall sensor 36 is activated, the controller 50 for controlling the sliding actuator 31 blocks the operation of the sliding actuator 31 to stop the moving body 110. Also, when the third hall sensor 37 is activated, the controller 50 operates the sliding actuator 31 so that the moving body 110 of the gas detector 100 being inserted into the receiving portion 11 of the device main body 10 is moved to the receiving position.

In the above description, the drive portion 30 is configured of the sliding actuator 31, for example, a piezoelectric motor. However, the structure of the drive portion 30 is not limited thereto. The drive portion 30 may be configured of an electric motor for generating a rotational movement.

Hereinafter, the drive portion to slidingly move the gas detector using the electric motor will be described in detail with reference to FIG. 9.

Figure 9:
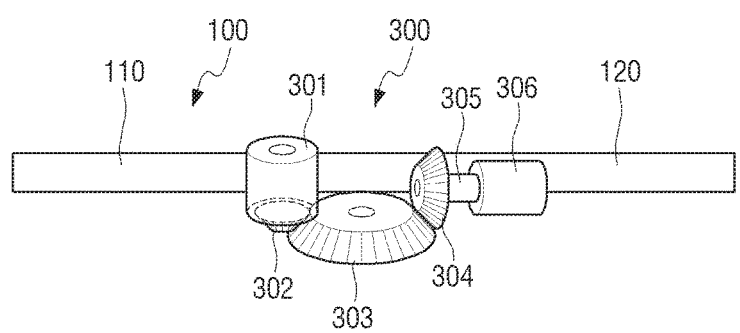
FIG. 9 is a view illustrating another example of a driving portion of a portable device having an exhalation sensing function according to an embodiment of the present disclosure.

FIG. 9 is a view illustrating another example of a driving portion of a portable device having an exhalation sensing function according to an embodiment of the present disclosure.

Referring to FIG. 9, a drive portion 300 may include a drive roller 301, a drive motor 306, and a plurality of bearings 33 (see FIG. 4A).

The drive roller 301 is disposed in the receiving portion 11 of the device main body 10, and is formed in contact with one side surface of the moving body 110 of the gas detector 100, thereby linearly moving the moving body 110. The drive roller 301 may be disposed to be in contact with and to press the moving body 110 at a predetermined pressure so that a frictional force is generated between the drive roller 301 and the moving body 110. The drive roller 301 may be formed of an elastic material such as rubber. A gear 302 may be provided in a lower end of the drive roller 301.

The drive motor 306 is an electric motor to generate a driving force capable of rotating the drive roller 301, and is disposed at a side of the receiving portion 11 of the device main body 10. A drive gear 304 is disposed in a motor shaft 305 of the drive motor 306. The drive gear 304 is connected with the gear 302 of the drive roller 301 via an intermediate gear 303. Accordingly, the rotational force of the drive motor 306 is transmitted to the gear 302 of the drive roller 301 through the drive gear 304 and the intermediate gear 303, thereby rotating the drive roller 301. When the drive roller 301 is rotated, the moving body 110 of the gas detector 100 is linearly moved.

The plurality of bearings 33 is provided opposite the drive roller 301 in the receiving portion 11 of the device main body 10, and supports the other side surface of the moving body 110. The plurality of bearings 33 is provided at a position facing the drive roller 301 to sandwich the moving body 110. The plurality of bearings 33 guides the linear movement of the moving body 110.

Accordingly, the controller 50 controls the drive motor 306 to project the gas detector 100 received in the receiving portion 11 of the device main body 10 to the outside of the device main body 10 or to return the projected gas detector 100 to the receiving position of the receiving portion 11. The drive portion 300 according to the present embodiment may include a position detecting portion for determining a position of the gas detector 100. The position detecting portion may be configured the same as the position detecting portion of the drive portion 30 of the above-described embodiment of the present disclosure. Therefore, a detailed description thereof is omitted.

The sliding actuator 31 and the drive motor 306 of the drive portions 30 and 300 are configured to be controlled by the controller 50 for controlling operation of the portable device 1. In other words, the controller 50 of the portable device 1 is configured to control the sliding actuator 31 and the drive motor 306 of the drive portions 30 and 300.

Hereinafter, a controller of a portable device having an exhalation sensing function according to an embodiment of the present disclosure to control a gas detector will be described with reference to FIG. 10.

Figure 10:
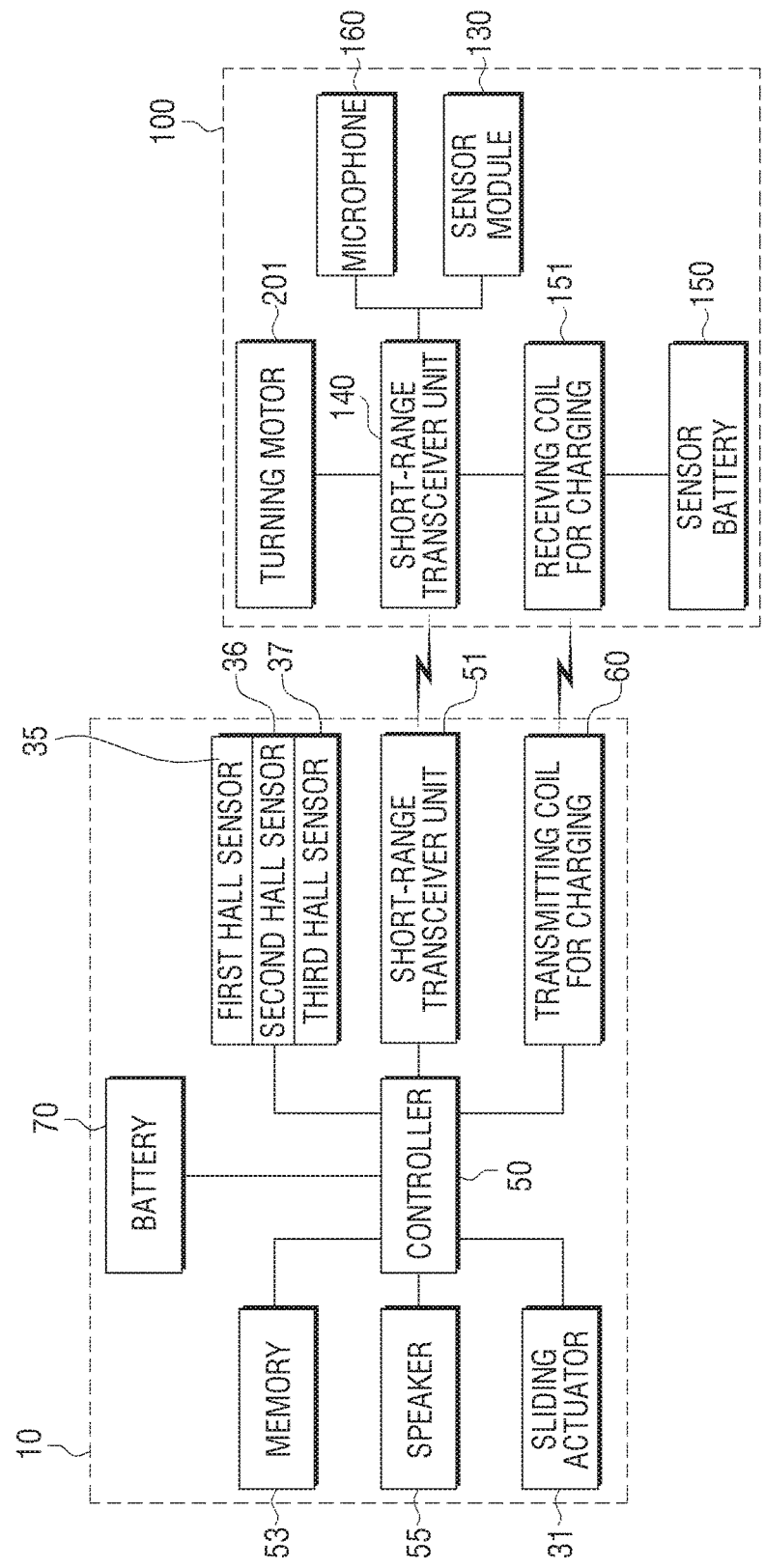
FIG. 10 is a functional block diagram illustrating a portable device having an exhalation sensing function according to an embodiment of the present disclosure.

FIG. 10 is a functional block diagram illustrating a portable device having an exhalation sensing function according to an embodiment of the present disclosure. In reference, the other components of the portable device are not illustrated in FIG. 10 because for the controller to control the other components is not related to the present disclosure.

The controller 50 controls as a whole the portable device 1, thereby allowing the portable device 1 to perform its functions.

The controller 50 provided in the device main body 10 may control the sliding actuator 31 and the drive motor 306 of the drive portions 30 and 300 so that the gas detector 100 is projected from the device main body 10 or returned to the original position. For example, when a user starts a telephone call, for example, the user operates a call button or a call icon provided in the device main body, the controller 50 drives the sliding actuator 31 or the drive motor 306 so that the gas sensor portion 120 of the gas detector 100 is projected from the device main body 10. Also, when the telephone call is terminated, for example, the user operates an end call button or an end call icon provided in the device main body, the controller 50 drives the sliding actuator 31 or the drive motor 306 so that the gas sensor portion 120 of the gas detector 100 is returned to the receiving position of the device main body 10.

Further, when the motor is disposed in the connecting portion between the moving body 110 and the gas sensor portion 120 of the gas detector 100, the controller 50 of the portable device 1 is configured to control the motor in the connecting portion to rotate the gas sensor portion 120 a certain angle.

Further, the controller 50 may be configured to control the sensor module 130 and the microphone 160 of the gas sensor portion 120 to measure exhalation of the user, to analyze components of the exhalation using the exhalation measurement data, and to make a comment in accordance with the analysis result.

The controller 50 may control the sensor module 130, the microphone 160, the turning motor 201, and the receiving coils for charging 151 and 152 provided in the gas sensor portion 120 of the gas detector 100 using the short-range transceiver unit 51 provided in the device main body 10 and the short-range transceiver unit 140 provided in the gas sensor portion 120 of the gas detector 100.

Further, the controller 50 is configured to determine the inserting direction of the gas detector 100 using the position detecting portion. For example, the gas detector 100 may be received in the normal state or the reversed state in the receiving portion 11 of the device main body 10. In detail, the gas detector 100 may be inserted into the receiving portion 11 of the device main body 10 so that, when the gas detector 100 is received in the receiving portion 11, one of two surfaces, that is, a first surface 110-1 and a second surface 110-2 of the gas detector 100 which are parallel to the display portion 20 of the device main body 10 is adjacent to the display portion 20.

Figure 11A:
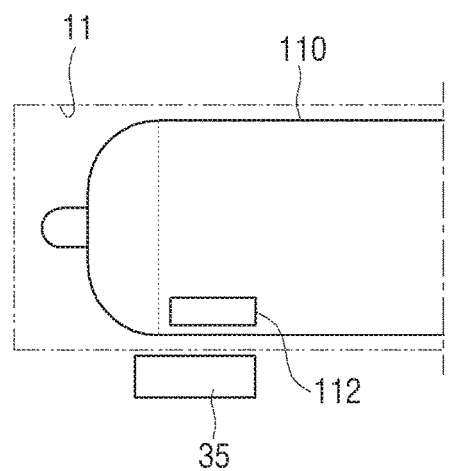
FIG. 11A is a view illustrating a case in which a permanent magnet of a gas detector of a portable device having an exhalation sensing function according to an embodiment of the present disclosure is inserted adjacent to a hall sensor.
Figure 11B:
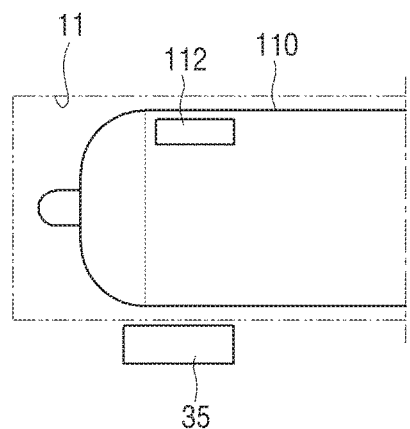
FIG. 11B is a case in which a permanent magnet of a gas detector of a portable device having an exhalation sensing function according to an embodiment of the present disclosure is inserted reversely to FIG. 11A.

FIG. 11A is a view illustrating a case in which a permanent magnet of a gas detector of a portable device having an exhalation sensing function according to an embodiment of the present disclosure is inserted so as to be adjacent to a hall sensor, and FIG. 11B is a view illustrating a case in which a permanent magnet of a gas detector of a portable device having an exhalation sensing function according to an embodiment of the present disclosure is inserted in the reverse of FIG. 11A.

Referring to FIG. 11A, when the gas detector 100 is inserted into the receiving portion 11 of the device main body 10 so that the permanent magnet 112 provided in the moving body 110 of the gas detector 100 is adjacent to the first hall sensor 35 (This is referred to as a normal insertion.), the first surface 110-1 of the gas detector 100 is adjacent to the display portion 20. Referring to FIG. 11B, when the gas detector 100 is inserted into the receiving portion 11 of the device main body 10 so that the permanent magnet 112 provided in the moving body 110 of the gas detector 100 is spaced away from the first hall sensor 35 (This is referred to as a reverse insertion.), the second surface 110-2 of the gas detector 100 is adjacent to the display portion 20.

When the gas detector 100 is the normal insertion, as illustrated in FIG. 11A, the permanent magnet 112 and the first hall sensor 35 are adjacent to each other so that a sensing voltage V1 of the first hall sensor 35 is high. When the gas detector 100 is the reverse insertion, as illustrated in FIG. 11B, the distance between the permanent magnet 112 and the first hall sensor 35 is farther than that of the normal insertion so that the sensing voltage V2 of the first hall sensor 35 is low. Accordingly, if using the sensing voltage coming from the first hall sensor 35, it may be determined whether the gas detector 100 is inserted in the normal state or the reverse state in the receiving portion 11 of the device main body 10.

Figure 11C:
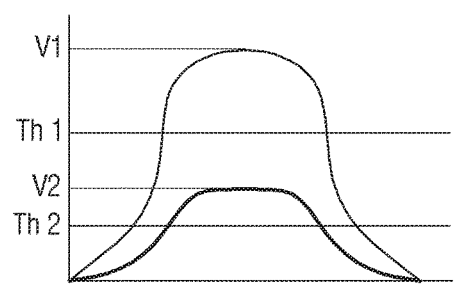
FIG. 11C is a graph illustrating a sensing voltage of the hall sensor of each of FIGS. 11A and 11B according to an embodiment of the present disclosure.

FIG. 11C is a graph illustrating a sensing voltage of the hall sensor of each of FIGS. 11A and 11B according to an embodiment of the present disclosure.

For example, referring to FIG. 11C, a first threshold value Th1 may be set to be smaller than the sensing voltage V1 of the first hall sensor 35 in the normal insertion, and larger than the sensing voltage V2 of the first hall sensor 35 in the reverse insertion. Further, a second threshold value Th2 may be set to be smaller than the sensing voltage V2 of the first hall sensor 35 in the reverse insertion. Here, FIG. 11C is a graph illustrating sensing voltages of the hall sensor of FIGS. 11A and 11B.

Accordingly, when the gas detector 100 is located in the receiving position, the controller 50 may determine whether the gas detector 100 is in the normal insertion or the reverse insertion based on the sensing voltage V of the first hall sensor 35. For example, if the sensing voltage V of the first hall sensor 35 is larger than the first threshold value Th1, the controller 50 determines that the gas detector 100 is in the normal insertion. If the sensing voltage V of the first hall sensor 35 is smaller than the first threshold value Th1 and larger than the second threshold value Th2, the controller 50 determines that the gas detector 100 is in the reverse insertion. The controller 50 determines the rotation direction of the gas sensor portion 120 according to the determination result, and then controls the turning motor 201 in the connecting portion of the gas detector 100 to rotate the gas sensor portion 120.

The portable device 1 having an exhalation sensing function according to an embodiment of the present disclosure having the above-described structure may sense and analyze the exhalation in two modes of use.

A first mode of use is that the portable device 1 automatically senses and analyzes exhalation of a user during a call in a state which the user does not perceive the sensing of the exhalation. A second mode of use is that the user consciously senses and analyzes the own exhalation using the portable device 1.

Hereinafter, the two modes of use of the portable device having an exhalation sensing function according to an embodiment of the present disclosure will be described in detail with reference to the accompanying drawings.

First, an operation in the first mode of use of the portable device having an exhalation sensing function will be described with reference to FIGS. 12 and 13.

Figure 12:
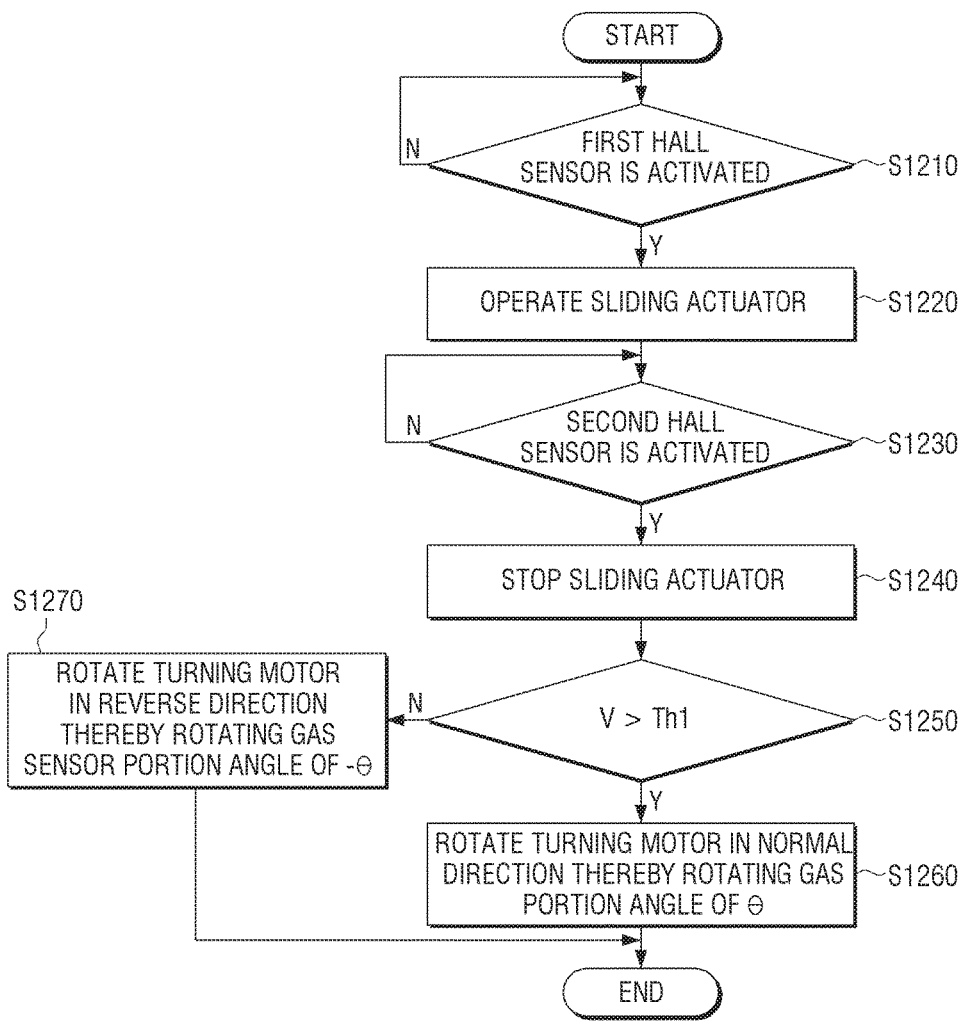
FIG. 12 is a flowchart illustrating a projecting operation of a gas detector of a portable device having an exhalation sensing function according to an embodiment of the present disclosure.

FIG. 12 is a flowchart illustrating a projecting operation of a gas detector of a portable device having an exhalation sensing function according to an embodiment of the present disclosure. FIG. 13 is a perspective view illustrating a state in which a gas detector projects when a user makes a call using a portable device having an exhalation sensing function according to an embodiment of the present disclosure.

The first mode of use may be set to be initiated in conjunction with the start of the phone call by the portable device 1. For example, if the portable device 1 is a smart phone, when the user touches a call icon, the controller 50 of the portable device 1 controls the sliding actuator 31 of the drive portion 30 to allow the gas sensor portion 120 of the gas detector 100 to be projected to the outside of the portable device 1.

Referring to FIG. 12, the controller 50 determines whether the first hall sensor 35 of the position detecting portion is activated at operation S1210. In detail, when the gas detector 100 is located in the receiving position of the device main body 10, the permanent magnet 112 of the gas detector 100 is located at a position facing the first hall sensor 35 so that the first hall sensor 35 is activated and outputs a sensing voltage. Accordingly, when the sensing voltage is output from the first hall sensor 35, the controller 50 determines that the gas detector 100 is located in the receiving position of the receiving portion 11 of the device main body 10. If the first hall sensor 35 is not activated, the controller 50 may perform a call operation regardless of the operation of the first hall sensor 35 depending on the setting condition. Alternatively, the controller 50 may inform the user that the gas detector 100 is not inserted in the device main body 10, and then standby.

When the first hall sensor 35 is determined to be operated, the controller 50 operates the sliding actuator 31 of the drive portion 30 at operation S1220. Then, the tip 32 of the sliding actuator 31 operates to cause the gas detector 100 to be linearly moved in a direction of arrow A (see FIG. 3). When the gas detector 100 is moved in the direction of arrow A, the gas sensor portion 120 of the gas detector 100 is projected to the outside through the opening 13 of the device main body 10.

The controller 50 determines whether the second hall sensor 36 is activated at operation S1230. When the second hall sensor 36 is activated, the controller 50 stops the sliding actuator 31 at operation S1240. Then, as illustrated in FIG. 5, the gas sensor portion 120 of the gas detector 100 is fully exposed to the outside of the device main body 10.

Next, the controller 50 determines whether the sensing voltage V of the first hall sensor 35 is larger than the first threshold value Th1 at operation S1250. When the sensing voltage V is larger than the first threshold value Th1, it is a state that the gas detector 100 is normally inserted into the receiving portion 11 of the device main body 10. Accordingly, the controller 50 controls the turning motor 201 provided in the connecting portion to rotate in a normal direction so that the gas sensor portion 120 is rotated a certain angle θ toward the display portion 20 of the portable device 1 at operation S1260. At this time, the controller 50 may control the turning motor 201 to rotate the gas sensor portion 120 about 40 to 50 degrees with respect to the moving body 110.

Figure 13:
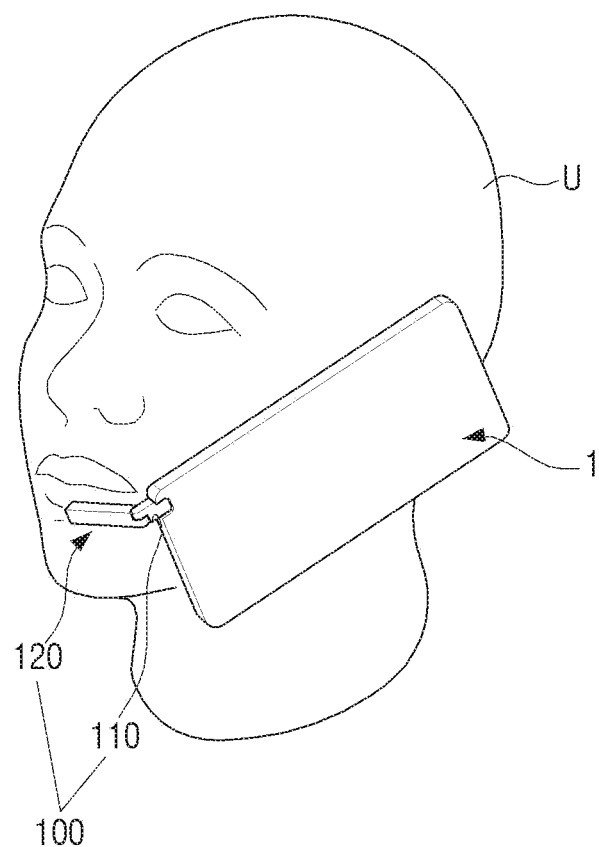
FIG. 13 is a perspective view illustrating a state in which a gas detector projects when a user makes a call using a portable device having an exhalation sensing function according to an embodiment of the present disclosure.

Then, referring to FIG. 13, the gas sensor portion 120 of the gas detector 100 is located near the mouth of the user U so that the gas sensor portion 120 can sense and analyze the user's exhalation coming out during a call.

When the sensing voltage V is smaller than the first threshold value Th1, it is a state that the gas detector 100 is reversely inserted into the receiving portion 11 of the device main body 10. Accordingly, the controller 50 controls the turning motor 201 provided in the connecting portion to rotate in a reverse direction so that the gas sensor portion 120 is rotated a certain angle θ toward the display portion 20 of the portable device 1 at operation S1270. Even when the gas detector 100 is reversely inserted into the device main body 10, the controller 50 rotates the gas sensor portion 120 in the opposite direction so that the gas sensor portion 120 is positioned near the user's mouth as illustrated in FIG. 13.

As described above, when using the portable device 1 having an exhalation sensing function according to an embodiment of the present disclosure, the gas sensor portion 120 provided with the sensor module 130 is positioned inclinedly within about 50 mm from the user's mouth so that the sensor module 130 can effectively sense and analyze the components of the exhalation coming out from the user's mouth during a call.

As describe above, with the portable device having an exhalation sensing function according to an embodiment of the present disclosure, when the user makes a call using the portable device 1, the gas detector 100 automatically projects from the receiving portion 11 of the device main body 10, thereby sensing the user's exhalation.

Further, with the portable device 1 having an exhalation sensing function according to an embodiment of the present disclosure, when the gas detector 100 is projected from the device main body 10, the projected portion of the gas detector 100, that is, the gas sensor portion 120 is inclined toward the user's mouth so that the gas sensor portion 120 can effectively sense the exhalation coming out from the user's mouth.

If the user drops the portable device 1 the gas sensor portion 120 of which is projected to the outside, the controller 50 may determine whether the portable device 1 is being dropped using a sensor, for example, an acceleration sensor included in the portable device 1, and rotate the turning motor 201 and the sliding actuator 31 in the opposite direction, thereby returning the gas detector 100 to the receiving portion 11 of the device main body 10.

Selection of the first mode of use as described above, that is, the mode in which the sensing of the exhalation is performed during a call may be configured to be performed by using a menu displayed on the display portion 20 of the portable device 1. For example, the user may select the first mode of use by selecting a check window outputting on a configuration setting screen or a phone call screen of the portable device 1.

Figure 14:
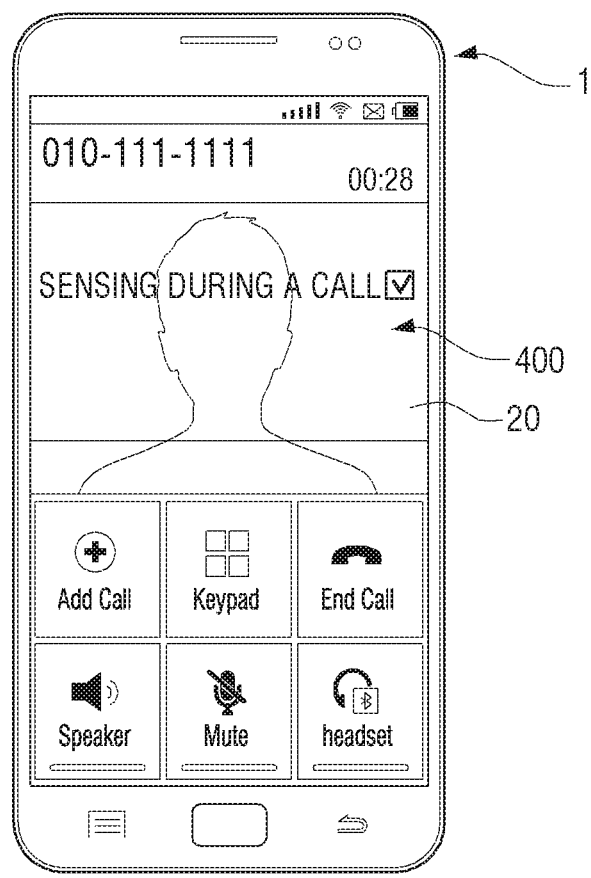
FIG. 14 is a view illustrating an exhalation sensing function selection screen of a portable device having an exhalation sensing function according to an embodiment of the present disclosure.

FIG. 14 is a view illustrating an exhalation sensing function selection screen of a portable device having an exhalation sensing function according to an embodiment of the present disclosure.

Referring to FIG. 14, when the user select the check window provided on a phone call screen 400, the user can use the first mode of use in which the exhalation is automatically sensed and analyzed during a call. Accordingly, when the window of the sensing during a call is checked, if the call icon is pressed or touched, the controller 50 automatically sticks out the gas sensor portion 120 of the gas detector 100, and senses the exhalation coming out from the user during a call, thereby obtaining data.

Hereinafter, an operation in the second mode of use of the portable device having an exhalation sensing function will be described in detail with reference to FIGS. 15, 16, and 17.

Figure 15:
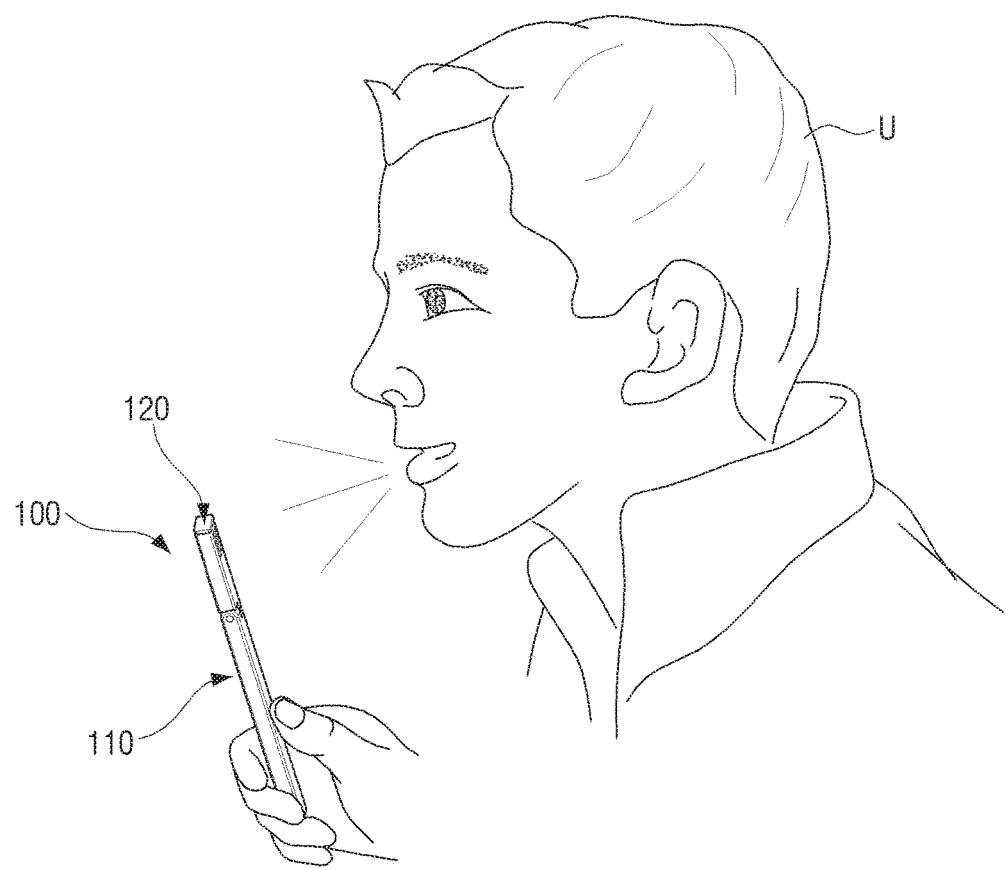
FIG. 15 is a view illustrating a state in which a user performs a precision measurement using a gas detector of a portable device having an exhalation sensing function according to an embodiment of the present disclosure.

FIG. 15 is a view illustrating a state of performing a precision measurement using a gas detector of a portable device having an exhalation sensing function according to an embodiment of the present disclosure. FIG. 16 is a view illustrating a sound waveform generated in a microphone of a gas detector of a portable device having an exhalation sensing function according to an embodiment of the present disclosure when a user exhales.

The second mode of use is used when a user wants to consciously analyze the exhalation using the portable device 1. At this time, referring to FIG. 15, after the user completely removes the gas detector 100 form the device main body 10, the user holds the moving body 110, and blows breath out to the gas sensor portion 120, thereby sensing components of the user's exhalation. Alternatively, regardless of the phone call, the user may stick out the gas sensor portion 120 of the gas detector 100 from the device main body 10, and sense the user's exhalation.

In the second mode of use, in order to increase the measurement accuracy of the gas sensor portion 120, the controller 50 may precisely control the strength of the user's blowing, the sensing start timing, and the sensing time by using the microphone 160 of the gas sensor portion 120.

Figure 16:
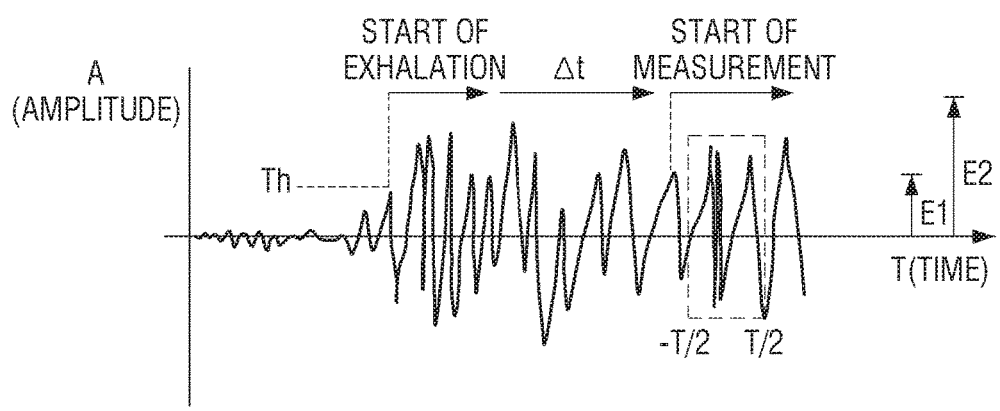
FIG. 16 is a view illustrating a sound waveform generated in a microphone of a gas detector of a portable device having an exhalation sensing function according to an embodiment of the present disclosure when a user blows breath out.

Referring to FIG. 16, when the user blows breath out to the gas sensor portion 120 of the gas detector 100, the microphone 160 of the gas sensor portion 120 outputs a sound signal. When the sound signal output from the microphone 160 exceeds a threshold value Th, the controller 50 may determine that the user blows breath out, and detect gas contained in the exhalation through the sensor module 130. At this time, the controller 50 may increase the sensing accuracy by adjusting the time for sensing gases of the exhalation by the sensor module 130.

For example, in order to increase the accuracy of the measured value of the exhalation, after initially removing the external air in the mouth, the measurement of the exhalation may be performed. In this case, the controller 50 may control the sensor module 130 to sense the exhalation after a certain period of time passes Δt after exhalation is started.

As another example, in order to detect gases in the alveolus, the measurement of the exhalation may be performed after removing the gas from the mouth to the airway. In this case, the controller 50 may control the sensor module 130 to sense the exhalation after a certain period of time (for example, about five seconds) passes after the user starts to blow breath out. In other words, since the controller 50 uses the microphone 160 to determine the start time of exhalation, the controller 50 may enhance the measurement accuracy or measure gases of a particular portion by adjusting the start time of sensing the exhalation.

Also, the controller 50 may measure the sound energy using the sound signal from the microphone 160 after the sensing of the exhalation is started, and then, may allow the user to blow breath out with a proper intensity. The energy E of the exhalation may be calculated from the amplitude of the sound signal as the following Equation.

$$E = \int_{A_{-T/2}}^{@^{T/2}} |A|^2 dt \qquad \text{Equation 1}$$

Accordingly, if the exhalation strength that is suitable for the sensor module 130 to measure the exhalation, that is, the energy of the exhalation E is E1≤E≤E2, the controller 50 determines the energy of the exhalation E from the sound signal of the microphone 160, and allows the user to blow breath out with an appropriate strength by notifying the user to blow harder or more weakly using sound, text, or image.

For example, when the appropriate energy E of the exhalation for sensing is E1≤E≤E2, if the energy of the exhalation E is less than E1, the controller 50 may inform the user "harder" by the sound through the speaker 55 of the portable device 1. If the energy of the exhalation E is greater than E2, the controller 50 may inform the user "more weakly" by the sound through the speaker 55 of the portable device 1.

As described above, when using the microphone 160 of the gas detector 100, because the strength and the sensing start time of the exhalation can be adjusted, the exhalation measurement using the microphone 160 may obtain a more precise measurement data compared to the exhalation measurement during a call.

After completing the precise measurement using the gas detector 100 separated from the device main body 10, the user inserts the gas detector 100 into the receiving portion 11 of the device main body 10, thereby keeping the gas detector 100 in the original state. When the gas detector 100 is inserted a predetermined length through the opening 13 of the device main body 10, the controller 50 detects the insertion of the gas detector 100, and then controls the sliding actuator 31 of the drive portion 30 so that the gas detector 100 may automatically be returned to the receiving position.

Hereinafter, an operation of the controller 50 to allow the gas detector 100 to be received in the receiving portion 11 of the device main body 10 will be described in detail with reference to FIG. 17.

Figure 17:
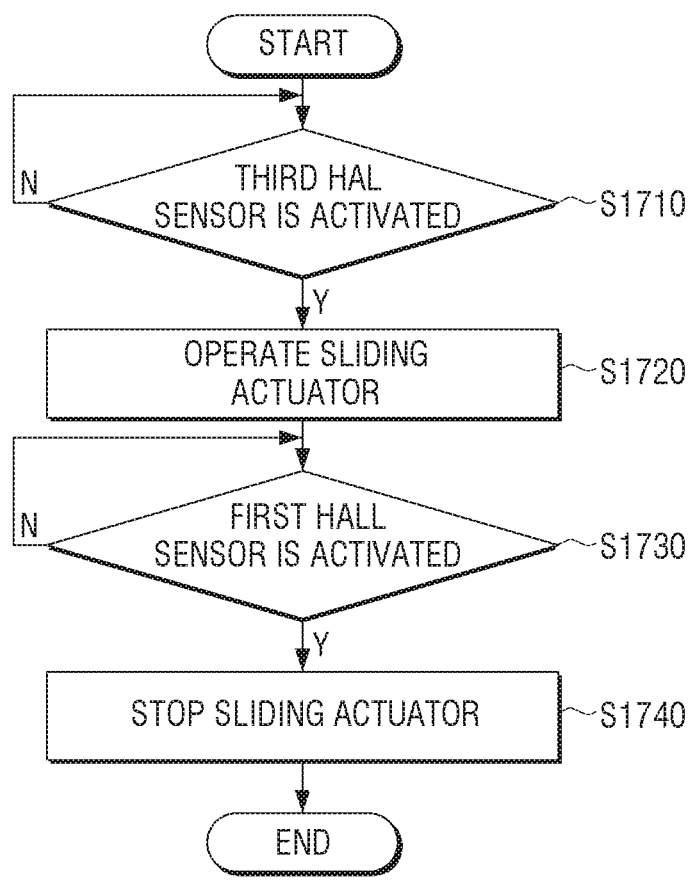
FIG. 17 is a flowchart illustrating an insertion operation of a gas detector of a portable device having an exhalation sensing function according to an embodiment of the present disclosure.

FIG. 17 is a flowchart illustrating an insertion operation of a gas detector of a portable device having an exhalation sensing function according to an embodiment of the present disclosure.

Referring to FIG. 17, the controller 50 determines whether the third hall sensor 37 of the position detecting portion is activated at operation S1710. If the third hall sensor 37 is activated, the controller 50 operates the sliding actuator 31 at operation S1720.

When the sliding actuator 31 is operated, the moving body 110 of the gas detector 100 is inserted into the receiving portion 11 of the device main body 10. At this time, the sliding actuator 31 operates in the opposite direction when allowing the gas detector 100 to be projected so that the gas detector 100 is inserted into the receiving portion 11.

Next, the controller 50 determines whether the first hall sensor 35 is activated at operation S1730. If the first hall sensor 35 is activated, the controller 50 stops the sliding actuator 31 at operation S1740. Thus, the gas detector 100 is completely inserted in the receiving portion 11 of the device main body 10 so that the front end of the gas detector 100 is not exposed to the outside of the device main body 10.

With the portable device 1 having an exhalation sensing function according to an embodiment of the present disclosure as described above, the user's exhalation may be automatically sensed and analyzed during a call, or the user's exhalation may be accurately sensed and analyzed by the user's selection.

Further, with the portable device 1 having an exhalation sensing function according to an embodiment of the present disclosure as described above, because the gas detector 100 may be separated from the portable device 1 and the microphone 160 is provided in the gas sensor portion 120 of the gas detector 100, in a place away from the portable device 1, external sounds, such as voice of another person, may be stored in a memory 53 of the device main body 10 using the microphone 160 of the gas detector 100.

The controller 50 may store the exhalation measurement data measured by the gas detector 100 in memory 53 by the measurement date and the measurement time.

Then, if necessary, according to a user's selection the controller 50 may output the stored exhalation measurement data in a graph form on the display portion 20. Also, the controller 50 may analyze the exhalation measurement data, and give the user a comment on the exhalation measurement data. The comment may be output by voice using the speaker 55 of the device main body 10.

Figure 18A:
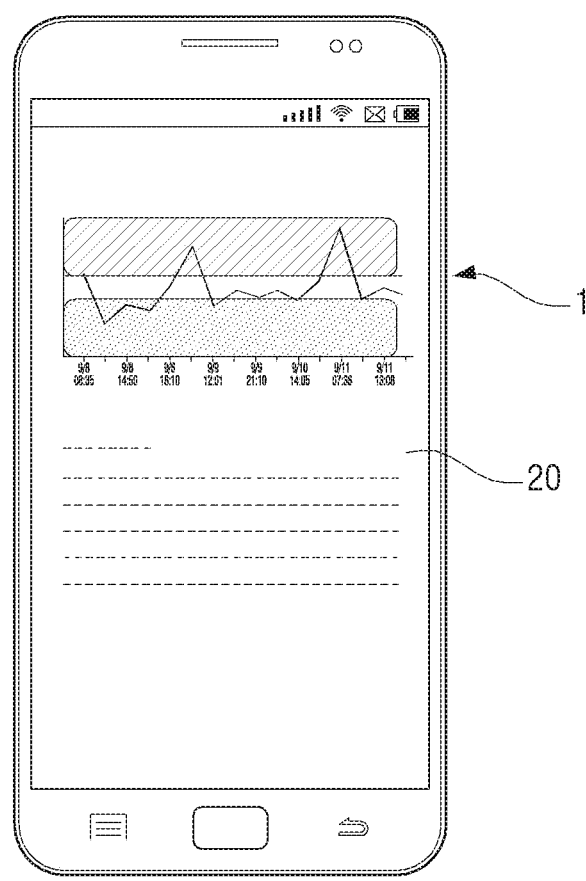
FIG. 18A is a view illustrating a state in which a graph of cumulative measurement data and comments of bad breath measured by a portable device having an exhalation sensing function according to an embodiment of the present disclosure is displayed.
Figure 18B:
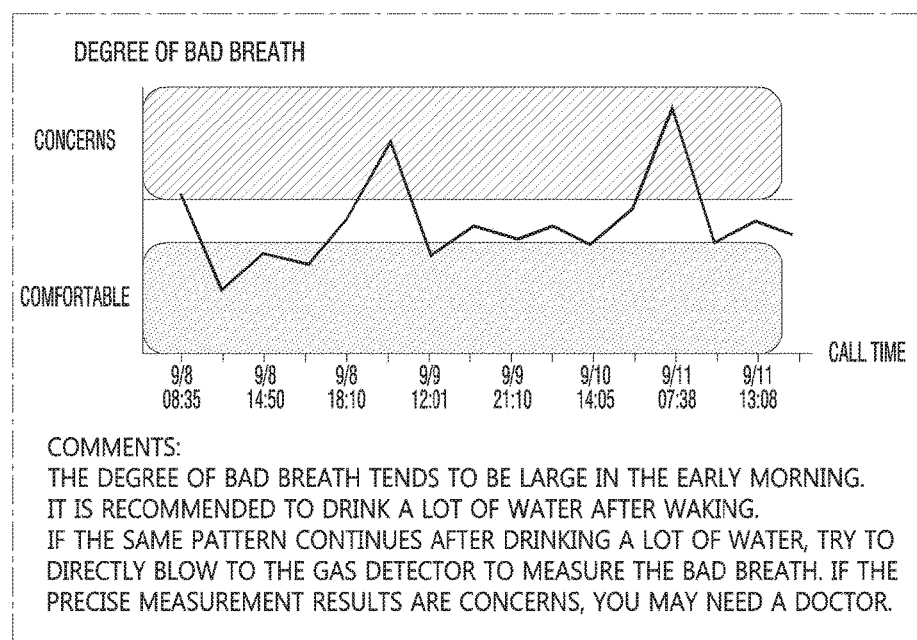
FIG. 18B is a view enlargedly illustrating the graph and comments of FIG. 18A according to an embodiment of the present disclosure.

FIGS. 18A and 18B illustrate an example of bad breath data measured by a gas detector of a portable device having an exhalation sensing function according to an embodiment of the present disclosure and a comment thereon.

FIG. 18A is a view illustrating a state in which a graph of cumulative measurement data and comments of bad breath are displayed on a portable device having an exhalation sensing function according to an embodiment of the present disclosure. FIG. 18B is a view enlargedly illustrating the graph and comments illustrated in FIG. 18A.

Referring to FIGS. 18A and 18B, the controller 50 of the portable device having an exhalation sensing function according to an embodiment of the present disclosure determines the degree of bad breath by automatically sensing and analyzing the user's exhalation whenever the user makes a call, and stores the result in the memory 53. Then, the controller 50 may display the bad breath measurement data in a graph form on the display portion 20 of the portable device 1 according to the user's request. So the user may easily know the degree of bad breath by call time through the graph.

The functions of the controller 50 that measures the user's exhalation, analyzes the measurement data, and outputs the measurement data, the analysis results, and comments may be created as program or application, thereby being installed in the portable device 1.

In the above description, an embodiment of the present disclosure is implemented as a portable device that is not foldable, for example, a smart phone. However, the present disclosure may be applied to foldable portable devices that can be folded.

Figure 19A:
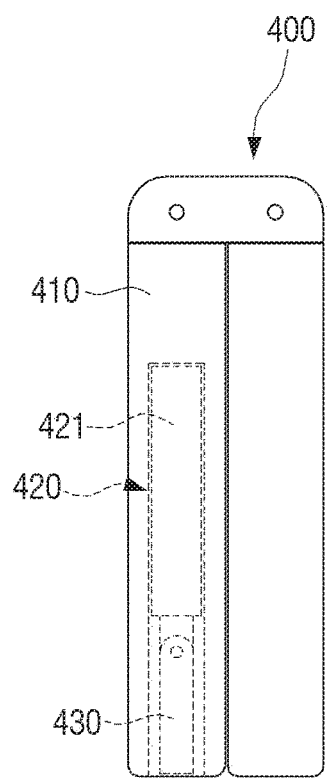
FIG. 19A is a view illustrating a state in which a foldable portable device is folded according to an embodiment of the present disclosure.
Figure 19B:
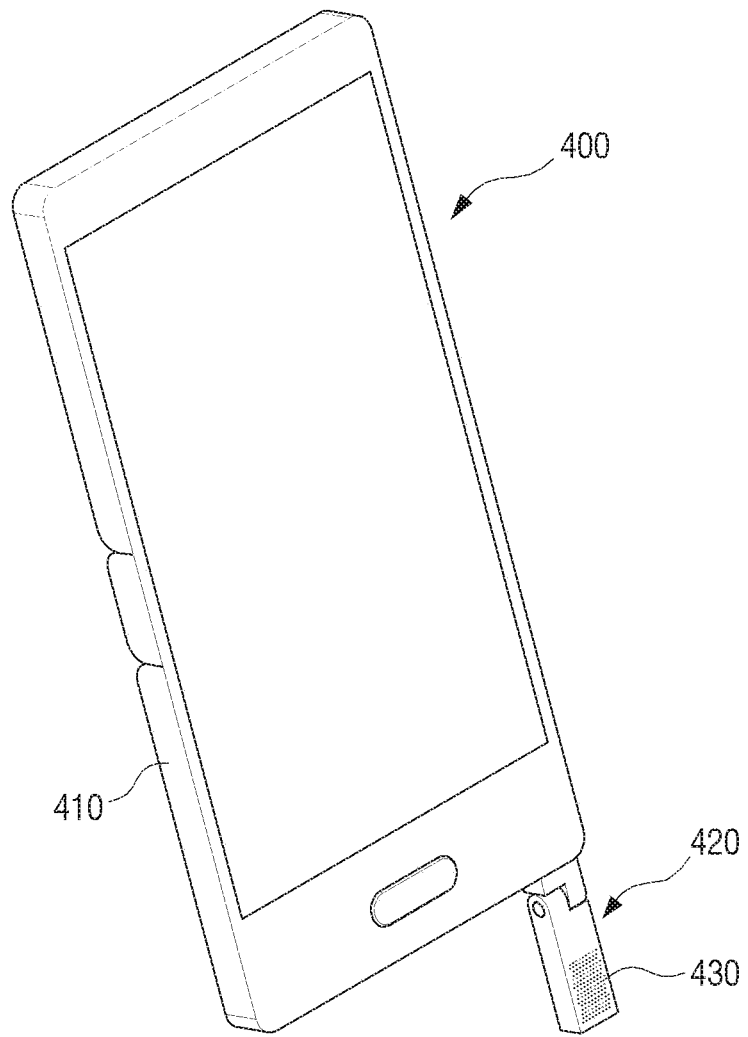
FIG. 19B is a view illustrating a state in which the foldable portable device of FIG. 19A is opened according to an embodiment of the present disclosure.

FIG. 19A is a view illustrating a state in which a foldable portable device is folded, and FIG. 19B is a view illustrating a state in which the foldable portable device of FIG. 19A is opened according to an embodiment of the present disclosure.

When no call, referring to FIG. 19A, the device main body 10 of the portable device 400 is folded. At this time, a gas detector 420 is received inside the device main body 410. Since the gas detector 420 is required to have a length shorter than the length of the above-described portable device 1, the moving body 421 of the gas detector 420 may be formed in a telescopic structure that permits lengthening or shortening as a telescopic antenna.

When making a call, referring to FIG. 19B, the gas sensor portion 430 of the gas detector 420 may automatically be projected and analyze a user's exhalation. At this time, operation of the gas sensor portion 430 of the gas detector 420 which is projected from the portable device 400 is the same as or similar to that of the gas detector 100 of the portable device 1 according to the above-described embodiment; therefore, a detailed description thereof is omitted.

Figure 20:
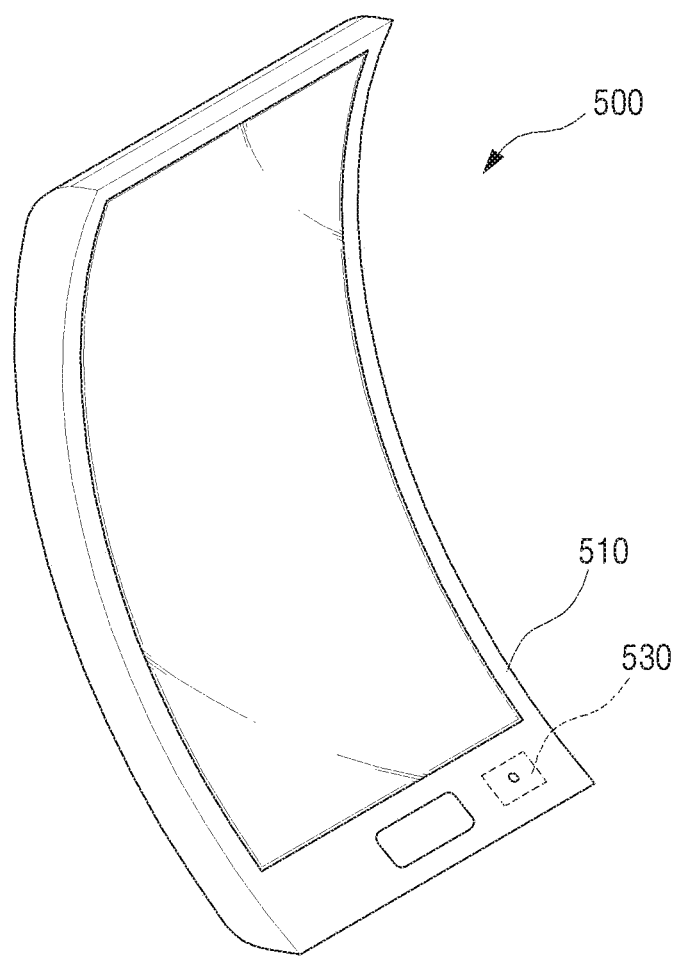
FIG. 20 is a perspective view illustrating a portable device a shape of which is changeable according to a user's face shape according to an embodiment of the present disclosure.

FIG. 20 is a perspective view illustrating a portable device a shape of which is changeable according to a user's face shape according to an embodiment of the present disclosure.

Referring to FIG. 20, as another example, when a portable device 500 has a structure in which the portable device 500 is automatically elongated to fit the shape of the user's face so that a mouthpiece portion 510 is located in front of the user's mouth, a gas sensor portion 530 may be provided in a side of the mouthpiece portion 510. In this case, since, when making a call, the gas sensor portion 530 is located in front of the user's mouth by the deformation of the portable device 500, it is not necessary to project the gas sensor portion 530 to the outside of the portable device 500.

In the above description, the gas sensor portion of the gas detector automatically analyzes the exhalation of the user during a call. However, the present disclosure is not limited thereto. As another example, a gas sensor portion may be provided in a variety of portable devices.

Hereinafter, various portable devices provided with a gas sensor portion will be described with reference to FIGS. 21 to 24.

Figure 21:
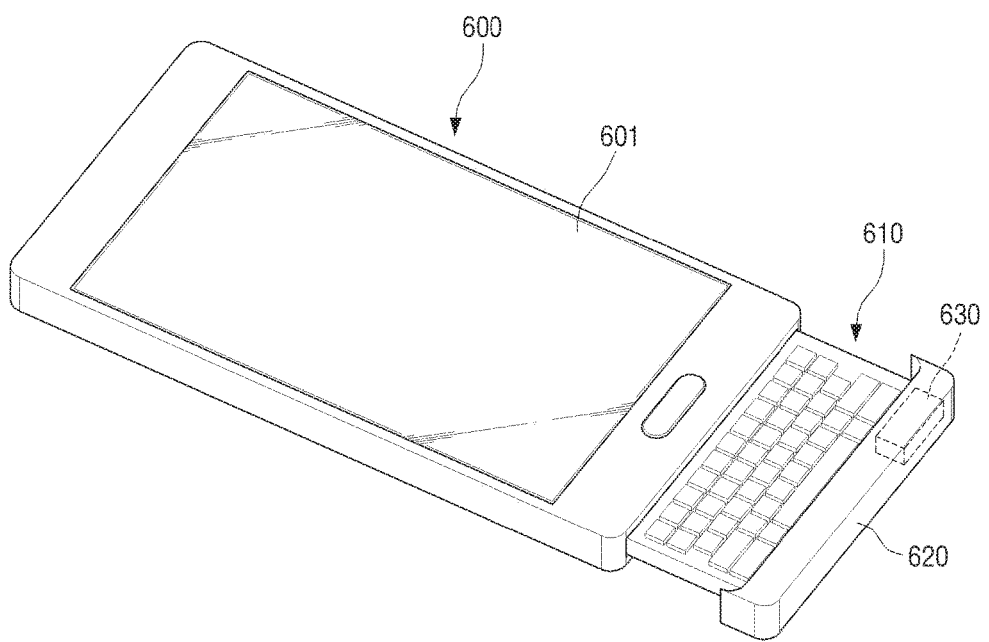
FIG. 21 is a perspective view illustrating a portable device having a slide keyboard with a built-in gas sensor portion according to an embodiment of the present disclosure.

FIG. 21 illustrates a portable device 600 having a slide keyboard 610 with a built-in gas sensor portion 630 according to an embodiment of the present disclosure.

Referring to FIG. 21, the gas sensor portion 630 is disposed inside a frame 620 of the slide keyboard 610. Accordingly, the user may analyze the exhalation or the quality of the external air around the portable device 600 using the gas sensor portion 630 provided in the slide keyboard 610. In particular, by using the microphone built in the gas sensor portion 630 the exhalation may be accurately analyzed. FIG. 21 shows a state in which the slide keyboard 610 is pull out from the device main body 601 in order to use the slide keyboard 610. The user may input data into the device main body 601 or control the device main body 601 through the slide keyboard 610.

Figure 22:
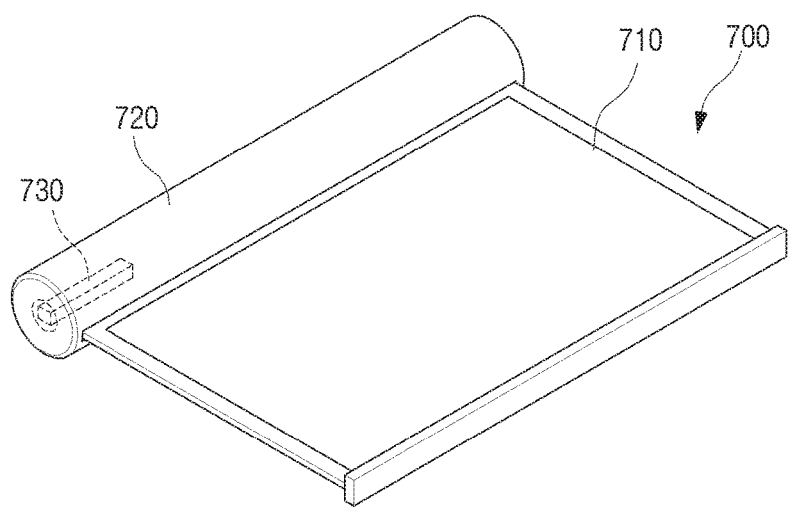
FIG. 22 is a perspective view illustrating a rollable portable device having a built-in gas senor portion according to an embodiment of the present disclosure.

FIG. 22 illustrates a rollable portable device 700 having a built-in gas sensor portion 730 according to an embodiment of the present disclosure.

Referring to FIG. 22, the rollable portable device 700 may include a display winding unit 720 of a cylindrical shape for winding and unwinding a flexible display 710. At this time, a gas sensor portion 730 may be provided in the display winding unit 720. The user may blow breath out to the center of the display winding unit 720, thereby measuring components of the user's exhalation. The user may measure the exhalation while the flexible display 710 is wound, and then, unwind the flexible display 710 so that the exhalation measurement results are displayed on the flexible display 710. Also, by using a microphone provided in the gas sensor portion 730 the exhalation may be precisely analyzed.

Figure 23:
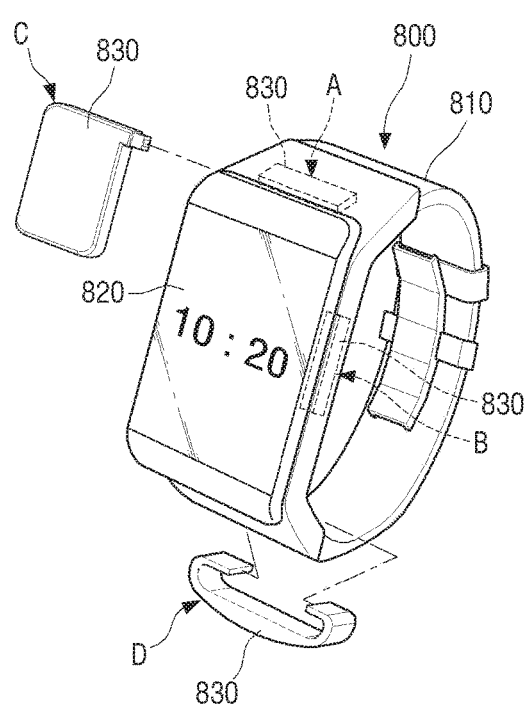
FIG. 23 is a perspective view illustrating a smart watch having a gas sensor portion according to an embodiment of the present disclosure.

FIG. 23 illustrates a gas sensor portion 830 provided in a portable device that is implemented as a smart watch 800 according to an embodiment of the present disclosure.

Referring to FIG. 23, the gas sensor portion 830 may be disposed in the smart watch 800 in a variety of forms. In FIGS. 23, A, B, C, and D denote a variety of forms of the gas sensor portions 830 which are disposed in the smart watch 800.

As illustrated in A, the gas sensor portion 830 may be disposed in one end of the display portion 820 of the smart watch 800 to which a strap 810 is connected. Alternatively, as illustrated in B, the gas sensor portion 830 may be disposed in a side portion of the display portion 820 of the smart watch 800 to which the strap 810 is not connected.

As another example, the gas sensor portion 830 may be implemented as a separate accessory. For example, as illustrated in C, the gas sensor portion 830 may be implemented as an accessory which is connected to the smart watch 800 by an electrical connector. Alternatively, the gas sensor portion 830 may be implemented as an accessory which is fixed to the strap 810. In this case, the gas sensor portion 830 may be configured to send and receive data with the smart watch 800 by using a short distance communication.

When the gas sensor portion 830 is built-in or externally mounted to the smart watch 800 as described above, the user may analyze his or her exhalation or the quality of surrounding air using the smart watch 800. Also, by using a microphone provided in the gas sensor portion 830, the exhalation analysis may be accurately performed.

When the gas sensor portion 630, 730, and 830 is built-in the portable device 600, 700, and 800 as described above, it is not necessary to move the gas sensor portion 630, 730, and 830. Therefore, the gas sensor portion 630, 730, and 830 may be implemented by a sensor module and a microphone. The sensor module and the microphone may be the same as or similar to the sensor module 130 and the microphone 160 of the gas sensor portion 120 of the portable device 1 according to the above-described embodiment of the present disclosure.

In the above explanation, the gas sensor portion is built-in the portable device. However, the gas sensor portion may be provided in an accessory of the portable device.

Hereinafter, accessories for a portable device provided with a gas sensor portion will be described with reference to FIGS. 24 to 26.

Figure 24:
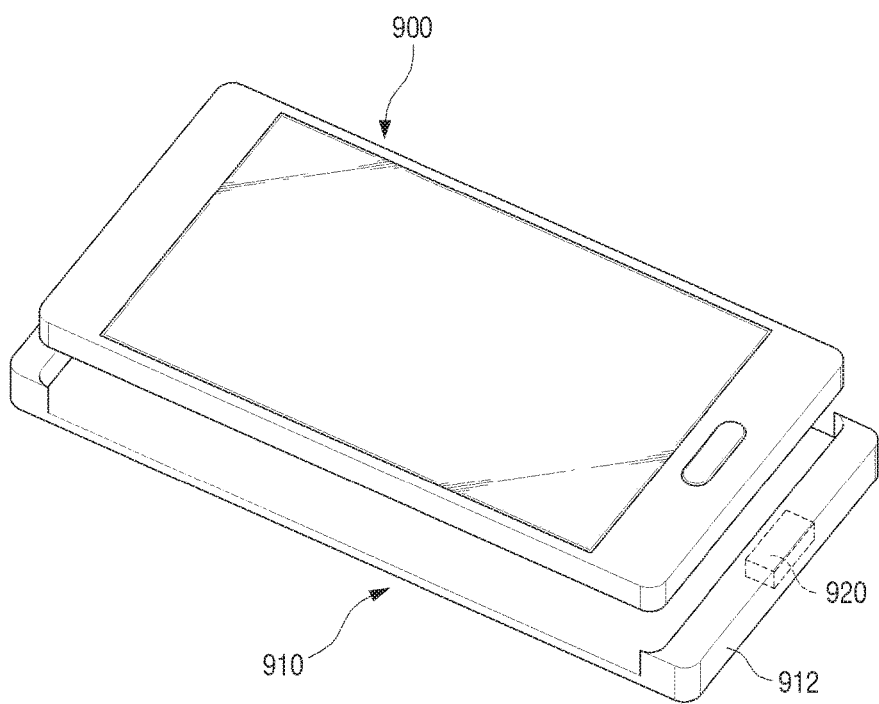
FIG. 24 is a perspective view illustrating a cover for a portable device provided with a built-in gas sensor portion according to an embodiment of the present disclosure.

FIG. 24 illustrates a cover 910 for a portable device 900 provided with a built-in gas sensor portion 920 according to an embodiment of the present disclosure.

Referring to FIG. 24, a gas sensor portion 920 is provided in a frame 912 of one end of a cover 910. When a secondary battery (not illustrated) is disposed in the frame 912 of the cover 910, the gas sensor portion 920 may be provided at a side of the secondary battery.

When the gas sensor portion 920 is provided in the cover 910 as described above, a user having a portable device 900 that is not provided with a gas sensor portion also can measure exhalation or the quality of the external air by using the gas sensor portion 920 provided in the cover 910. At this time, the user needs to install an application or program to control the gas sensor portion 920 provided in cover 910 in the portable device 900. Also, by using a microphone provided in the gas sensor portion 920 the user may accurately perform the exhalation analysis. By using the microphone of the cover 910 as an external microphone external sounds may be recorded in the portable device 900.

Figure 25:
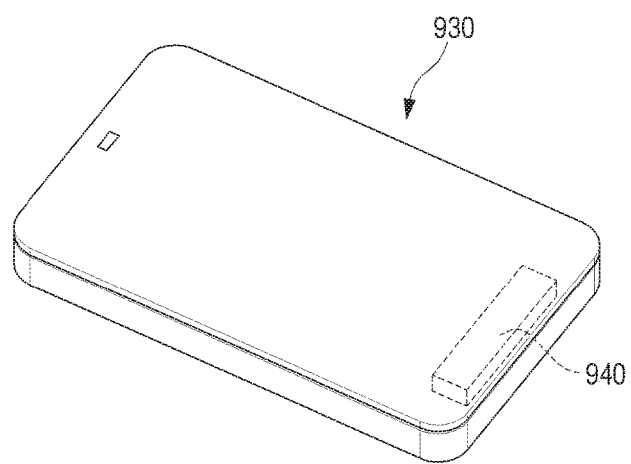
FIG. 25 is a perspective view illustrating a secondary battery with a built-in gas sensor portion according to an embodiment of the present disclosure.

FIG. 25 illustrates a gas sensor portion 940 provided in a secondary battery 930 for charging a portable device according to an embodiment of the present disclosure.

Referring to FIG. 25, a gas sensor portion 940 is provided in one side of the inside of the secondary battery 930. FIG. 25 illustrates a state in which the gas sensor portion 940 is provided in one end of the secondary battery 930. The installation position of the gas sensor portion 940 is not limited thereto. The gas sensor portion 940 may be provided in any place of one side, the upper surface, and the bottom surface of the secondary battery 930.

When the gas sensor portion 940 is provided in the secondary battery 930 as described above, a user having a portable device that is not provided with a gas sensor portion also can measure exhalation or the quality of the external air by using the gas sensor portion 940 provided in the secondary battery 930. At this time, the user needs to install an application or program for controlling the gas sensor portion 940 provided in the secondary battery 930 in the portable device. Also, by using a microphone provided in the gas sensor portion 940 the user may accurately perform the exhalation analysis. By using the secondary battery 930 provided with the gas sensor portion 940 having the microphone as an external microphone, external sounds may be recorded in the portable device.

Figure 26:
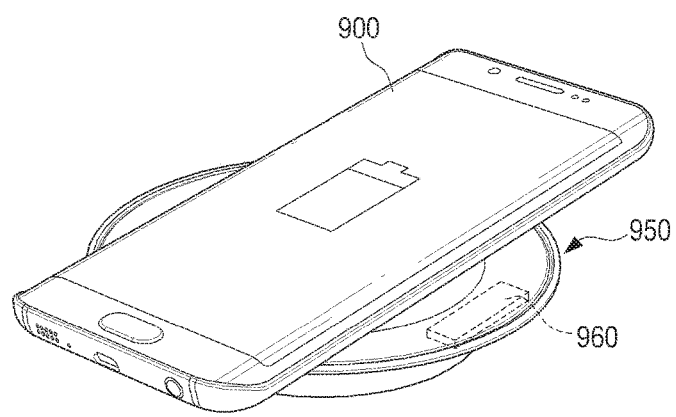
FIG. 26 is a perspective view illustrating a wireless charging station with a built-in gas sensor portion according to an embodiment of the present disclosure.

FIG. 26 illustrates a wireless charging station 950 for charging a portable device 900 with a built-in gas sensor portion 960 according to an embodiment of the present disclosure.

Referring to FIG. 26, a gas sensor portion 960 is provided in a wireless charging station 950. The gas sensor portion 960 may be disposed in any position in the wireless charging station 950. FIG. 26 illustrates a case in which the gas sensor portion 960 is built-in the wireless charging station 950. Although not illustrated, the gas sensor portion 960 may be provided in a wired charger or a wired charging station.

When the gas sensor portion 960 is provided in the wireless charging station 950 as described above, the user may measure his or her exhalation using the gas sensor portion 960 while charging the portable device 900. Also, the gas sensor portion 960 provided in the wireless charging station 950 may analyze the air quality in a place where the wireless charging station 950 is placed, and remotely inform the user about the analysis result. At this time, the user needs to install an application or program for controlling the gas sensor portion 960 provided in the wireless charging station 950 in the portable device 900. Also, by using a microphone provided in the gas sensor portion 960 the user may accurately perform the exhalation analysis. By using the microphone of the gas sensor portion 960 provided in the wireless charging station 950 as an external microphone, sounds being generated in a place where the wireless charging station 950 is disposed may be recorded in the portable device 900.

The gas sensor portions 920, 940, and 960 used in the above-described embodiments may be formed similar to the gas sensor portion 120 of the above-described portable device 1. Accordingly, the gas sensor portion 920, 940, and 960 may include a sensor module, a microphone, a sensor battery, and a receiving coil for charging. However, since it is not necessary to move the gas sensor portion 920, 940, and 960, the drive motor is not provided. The sensor module, the microphone, the sensor battery, and the receiving coil for charging of the gas sensor portion 920, 940, and 960 may be the same as or similar to the sensor module 130, the microphone 160, the sensor battery 150, and the receiving coils for charging 151 and 152 of the gas sensor portion 120 of the portable device 1 according to the above-described embodiment; therefore, detailed description thereof is omitted.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A portable device having an exhalation sensing function, the portable device comprising:
    a gas detector configured to analyze a user's exhalation; and
    a device main body including a receiving portion in which the gas detector is received, the device main body having a call function that is executed in response to a user input on a call button or a call icon of the device main body,
    wherein, the gas detector, in response to the user input on the call button or the call icon of the main body, is further configured to:
        be automatically projected from the receiving portion of the device main body, and
        sense the user's exhalation.

2. The portable device of claim 1, wherein when the gas detector is projected from the device main body, a projecting portion of the gas detector is inclined toward a mouth of the user.

3. The portable device of claim 1, wherein the gas detector is configured to project from a side of a mouthpiece portion of the device main body.

4. The portable device of claim 3, wherein the gas detector comprises:
    a moving body slidingly disposed in the receiving portion of the device main body, and
    a gas sensor portion rotatably disposed in the moving body,
    wherein the device main body comprises a drive portion to move the moving body with respect to the receiving portion of the device main body, and
    wherein when the gas detector is projected from the receiving portion of the device main body by the drive portion, the gas sensor portion is rotated a predetermined angle toward the mouthpiece portion of the device main body.

5. The portable device of claim 4, wherein the gas sensor portion comprises:
    a sensor module that analyzes the exhalation,
    a short-range transceiver unit that transmits data measured by the sensor module to the device main body,
    a sensor battery that supplies an electric power to the sensor module and the short-range transceiver unit, and
    a housing that receives the sensor module, the short-range transceiver unit, and the sensor battery, the housing rotatably connected to the moving body.

6. The portable device of claim 5,
    wherein the gas sensor portion comprises a receiving coil for charging that charges the sensor battery, and
    wherein the device main body is provided with a transmitting coil for charging that supplies electricity to the receiving coil for charging.

7. The portable device of claim 6, wherein when a battery of the device main body is charged, the transmitting coil for charging supplies electricity to the receiving coil for charging, thereby charging the sensor battery.

8. The portable device of claim 5, wherein the gas sensor portion comprises a microphone for measuring strength of the exhalation.

9. The portable device of claim 5, wherein the sensor module comprises at least one of a bad breath detection sensor, an alcohol detection sensor, a carbon monoxide detection sensor, a carbon dioxide detection sensor, a volatile organic compounds (VOCs) detection sensor, and a volatile sulfide compounds (VSCs) detection sensor.

10. The portable device of claim 4, wherein the gas sensor portion is configured to be rotated with respect to the moving body by a motor.

11. The portable device of claim 4, wherein a torsion spring is disposed between the gas sensor portion and the moving body.

12. The portable device of claim 4, wherein the drive portion comprises: a sliding actuator disposed at a side of the moving body in the device main body, a plurality of bearings disposed opposite the sliding actuator in the device main body, and a plurality of elastic members disposed to press the plurality of bearings toward the moving body.

13. The portable device of claim 12, wherein the drive portion comprises a position detecting portion for detecting a position of the moving body.

14. The portable device of claim 12, wherein a guide member is disposed on a side surface of the moving body that is in contact with the sliding actuator.

15. The portable device of claim 4, wherein the drive portion comprises:
    a drive roller that is disposed in the device main body and pressed in contact with one side surface of the moving body, a drive motor that rotates the drive roller, and a plurality of bearings that is disposed opposite the drive roller in the device main body and supports the moving body.

16. The portable device of claim 4,
    wherein the device main body comprises a controller for controlling the portable device, and
    wherein when a call button or icon provided in the device main body is operated, the controller controls the drive portion to project the gas detector from the device main body.

17. The portable device of claim 16, wherein the device main body comprises a display portion for displaying information, and wherein the controller outputs an analysis result of the exhalation detected by the gas detector to the display portion.

18. The portable device of claim 17,
    wherein the device main body comprises a memory for storing measurement data of the exhalation, and
    wherein the controller outputs exhalation measurement data of a certain period of time that is stored in the memory and comments for the exhalation measurement data to the display portion.

19. The portable device of claim 4, wherein the moving body comprises a stylus pen or a thermometer.

20. A mobile phone device comprising:
    a gas detector; and
    a main body including a receiving portion in which the gas detector is received, the main body having a call function that is executed in response to a user input on a call button or a call icon of the main body,
wherein, the main body, in response to receiving the user input on the call button or the call icon, is configured to:
  automatically project the gas sensor from the receiving portion of the main body,
  perform an exhalation sensing function; and
  analyze the sensed exhalation, and
wherein the main body is foldable.

* * * * *